US009037216B2

(12) United States Patent
Hielscher et al.

(10) Patent No.: US 9,037,216 B2
(45) Date of Patent: May 19, 2015

(54) SYSTEMS AND METHODS FOR DYNAMIC IMAGING OF TISSUE USING DIGITAL OPTICAL TOMOGRAPHY

(75) Inventors: Andreas H. Hielscher, Brooklyn, NY (US); Yang Li, New York, NY (US); Andres Bur, New York, NY (US); Molly Flexman, New York, NY (US); James Masciotti, Denwood, MD (US); Christopher J. Fong, Elk Grove, CA (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 579 days.

(21) Appl. No.: 12/832,780

(22) Filed: Jul. 8, 2010

(65) Prior Publication Data

US 2010/0292569 A1    Nov. 18, 2010

Related U.S. Application Data

(63) Continuation-in-part of application No. PCT/US2009/037285, filed on Mar. 16, 2009.

(60) Provisional application No. 61/036,650, filed on Mar. 14, 2008, provisional application No. 61/158,915, filed on Mar. 10, 2009.

(51) Int. Cl.
*A61B 5/05* (2006.01)
*A61B 6/00* (2006.01)
(Continued)

(52) U.S. Cl.
CPC .................................... *A61B 5/0073* (2013.01)

(58) Field of Classification Search
USPC .................. 600/407, 425, 476, 473; 382/128
See application file for complete search history.

(56) References Cited

U.S. PATENT DOCUMENTS 4,800,574 A * 1/1989 Tanaka et al. .................. 375/243
7,463,362 B2 * 12/2008 Lasker et al. .................. 356/497
(Continued)

OTHER PUBLICATIONS

Rosa et al., "A Master-Slave DSP Board for Digital Control", Online: http://web.archive.org/web/20040821154712/http://www.ti.com/sc/docs/general/dsp/fest99/digital_control/9p_dspfest.pdf, Online availability on Aug. 8, 2004.*

(Continued)

*Primary Examiner* — Katherine Fernandez
(74) *Attorney, Agent, or Firm* — Miles & Stockbridge P.C.; Mark A. Catan

(57) ABSTRACT

A methods for imaging tissue using diffuse optical tomography with digital detection includes directing at the tissue a plurality of amplitude modulated optical signals from a plurality of optical signal sources illuminating the tissue at a plurality of locations; detecting a resulting plurality of attenuated optical signals exiting the tissue to obtain a plurality of analog signals containing diffuse optical tomographic information; converting the analog signals into digital signals; recovering the tomographic information from the digital signals using a digital signal processor-based detection module that performs digital detection, wherein the detection module includes a master digital signal processing subsystem and at least one slave digital signal processing subsystem that processes at least a portion of the digital signals and the master digital signal processing subsystem controls the at least one slave digital signal processing subsystem; and transmitting the recovered tomographic information in digital form to a host computer.

49 Claims, 19 Drawing Sheets

(51) Int. Cl.
*G06K 9/00* (2006.01)
*A61B 5/00* (2006.01)

(56) References Cited

U.S. PATENT DOCUMENTS

| | | | |
|---|---|---|---|
| 7,728,986 B2* | 6/2010 | Lasker et al. | 356/497 |
| 2004/0039268 A1* | 2/2004 | Barbour et al. | 600/310 |
| 2005/0243322 A1* | 11/2005 | Lasker et al. | 356/432 |
| 2006/0077395 A1 | 4/2006 | Chan et al. | |

OTHER PUBLICATIONS

A. H. Hielscher, A. Y. Bluestone, G. S. Abdoulaev, A. D. Klose, J. M. Lasker, M. Stewart, U. Netz, and J. Beuthan, "Near-infrared diffuse optical tomography," Disease Markers vol. 18, 313 (2002).

C. H. Schmitz, D. P. Klemer, R. Hardin, M. S. Katz, Y. Pei, H. L. Graber, M. B. Levin, R. D. Levina, N. A. Franco, W. B. Solomon, and R. Barbour, "Design and implementation of dynamic near-infrared optical tomographic imaging instrumentation for simultaneous dual-breast measurements," Applied Optics vol. 44, 2140 (2005).

C. H. Schmitz, M. Locker, J. M. Lasker, A. H. Hielscher, and R. Barbour, "Instrumentation for fast functional optical tomography," Review of Scientific Instruments vol. 73, 429 (2002).

C. Li, H. Zhao, B. Anderson, and H. Jiang, "Multispectral breast imaging using a ten-wavelength, 64X64 source/detector channels silicon photodiode-based diffuse optical tomography system," Medical Physics vol. 33, 627 (2006).

D. Piao, H. Dehghani, S. Jiang, S. Srinivasan, and Brian W. Pogue, "Instrumentation for video-rate near-infrared diffuse optical tomography," Review of Scientific Instruments vol. 76, 124301 (2005).

G. Gulsen, B. Xiong, O. Birgul, and O. Nalcioglu, "Design and implementation of a multifrequency near-infrared diffuse optical tomography system," Journal of Biomedical Optics vol. 11, 014020 (2006).

H. Dehghani, B. W. Pogue, S. P. Poplack, and K. D. Paulsen, "Multiwavelength three-dimensional near-infrared tomography of the breast: initial simulation, phantom, and clinical results," Applied Optics vol. 42, 135 (2003).

H. Jiang, Y. Xu, N. Iftimia, J. Eggert, K. Klove, L. Baron, and L. Fajardo, "Three-dimensional optical tomographic imaging of breast in a human subject," IEEE Trans. Med. Imaging vol. 20, 1334(2001).

J. M. Lasker, J. M. Masciotti, Y. Li, C. Fong, and Andreas H. Hielscher, "Dynamic optical tomographic imager with optimized digital lock-in filtering," Proc. SPIE OSA Biomedical Optics vol. 6629, 662903-1 (2007).

M. A. Franceschini, K. T. Moesta, S. Fantini, G. Gaida, E. Gratton, H. Jess, W. W. Mantulin, M. Seeber, P. M. Schlag, and M. Kaschke, "Frequency-domain techniques enhance optical mammography: initial clinical results," Proc. Natl. Acad. Sci. U.S.A. 94, 6468 (1997).

S. B. Colak, M. B. van der Mark, G. W. 't Hooft, J. H. Hoogenraad, E. S. van der Linden, and F. A. Kuijpers, "Clinical optical tomography and NIR spectroscopy for breast cancer detection," IEEE J. Sel. Top. Quantum Electron. vol. 5, 1143 (1999).

S. Fantini, S. A. Walker, M. A. Franceschini, M. Kaschke, P. M. Schlag, and K. T. Moesta, "Assessment of the size, position, and optical properties of breast tumors in vivo by noninvasive optical methods," Applied Optics vol. 37, 1982 (1998).

International Search Report and Written Opinion for corresponding U.S. Patent Application No. PCT/US2009/037285.

* cited by examiner

DSP-Imaging Routine

600

602 — Use a Digital Lock-In Filter with the following constraints that is ideal for discrimination of frequency encoded sources (different wavelength λ)

$$f_{\lambda i} = m_i \frac{f_s}{K}$$

$f_{\lambda i}$ = Modulation frequency
$f_s$ = ADC sampling frequency
K = Number of samples per source
$m_i$ = integer    $1 < m_i < K/2$
Filter Settling time $T_F = K/f_s$
   use $f_s$ = 75 KHz, K = 150 samples
$f_{\lambda i} = m_i * .5$ KHz, $T_F$ = 2 ms 604 — The algorithm extracts from the measured signal M[k], the amplitude $A_{\lambda i}$ of the component due to wavelength λi.

606 — Store K values for cosine and sine wave at frequencies $f_{\lambda i}$.

608 — Modulate M[k] by the stored signals and then pass through an averaging filter.

610 — Use quadrature rule to produce phase shift independent amplitude.

$$I_{\lambda i} = \frac{1}{K} \sum_{k=1}^{K} \left( M[k] \cos\left[ 2\pi \frac{f_{\lambda i}}{f_s} k \right] \right),$$

$$Q_{\lambda i} = \frac{1}{K} \sum_{k=1}^{K} \left( M[k] \sin\left[ 2\pi \frac{f_{\lambda i}}{f_s} k \right] \right),$$

$$A_{\lambda i} = 2\sqrt{I_{\lambda i}^2 + Q_{\lambda i}^2}.$$

Lock-In Algorithm

Fig. 6

SYSTEMS AND METHODS FOR DYNAMIC IMAGING OF TISSUE USING DIGITAL OPTICAL TOMOGRAPHY

RELATED APPLICATION

This application is a PCT Continuation-in-part application of International Patent Application No. PCT/US2009/037285, filed Mar. 16, 2009, which claims the benefit under 35 U.S.C. §119(e) of U.S. Provisional Patent Application No. 61/036,650, filed Mar. 14, 2008, and U.S. Provisional Patent Application No. 61/158,915, filed Mar. 10, 2009, each of which is hereby incorporated by reference herein in its entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

The disclosed subject matter relates to systems and methods for imaging tissue using diffuse optical tomography with digital detection.

BACKGROUND

Diffuse optical tomography, also referred to as optical tomographic imaging, is often performed by measuring the amplitude attenuation of light that has been passed through tissue. Propagation of injected photons is determined by the spatially-varying absorption and scattering characteristics of the tissue being probed. In biological tissues, scattering interactions are often the principal mechanisms affecting the light trajectory. As a result of this highly scattering nature, these photons do not navigate in a straight procession but rather diffuse throughout the medium. The photon flux exiting the tissue at any single point is the net effect of the incident light source, and discrete absorption and scattering interactions throughout their pathlength.

By illuminating several locations around the tissue of interest, and detecting transmitted and back-reflected intensities at multiple positions along the surface, one can generate tomographic images, similar to X-ray computed tomography. The transmitted intensity measured along the target surface maintains the same frequency with respect to the source. However, the measured intensity will exhibit an amplitude attenuation and an induced phase shift. This amplitude attenuation and phase shift provide spatial information regarding the absorption and scattering distribution inside the tissue.

In continuous wave imaging, the light is either illuminated at a constant amplitude or modulated by a low frequency sine wave (up to a few kHz), and the decay in amplitude relative to the incident source is measured. If the illuminated source is modulated, then a synchronous or homodyne detection technique is often employed to extract the zero-frequency amplitude information. This method requires generating a reference signal whose frequency is equal to and phase locked with the input waveform. Multiplying the input waveform by its reference signal produces an output waveform that is a composite of two independent contributions; one component located at zero-frequency and the other component straddling twice the modulation frequency.

This resulting mixed signal is then sent through a low-pass filter to eliminate the higher frequency component, leaving only the remaining DC constituent whose amplitude is directly proportional to the amplitude of the detected optical signal. By imaging with multiple wavelengths, the spectral information is increased allowing investigators to formulate qualitative assessments of hemoglobin parameters such as oxyhemoglobin and deoxyhemoglobin, or quantitative valuations of additional physiologic chromophores. Each wavelength must be modulated at distinct frequencies and/or phase in order to isolate the individual signals and their respective amplitudes.

Almost all continuous-wave optical tomography systems currently cited in literature perform any relevant signal conditioning and data processing through analog techniques, such as described in C. H. Schmitz, M. Locker, J. M. Lasker, A. H. Hielscher, R. L. Barbour, "Instrumentation for fast functional optical tomography," Review of Scientific Instruments, Vol. 73, pp. 429-439 (2002), which is hereby incorporated by reference herein in its entirety (which publication is hereinafter referred to as "Schmitz 2002"). Analog systems are used to collect, condition, and possibly filter the incident signal. For those instruments that modulate the intensity of their light source, analog phase-sensitive lock-in methods are usually employed to extricate the optical signal obscured by noise of potentially greater magnitude.

Such analog detection systems, however, suffer from a number of deficiencies and limitations. More specifically, for example, analog phase-sensitive detection has many problems associated with it that adversely affect their performance and restrict subsequent applications. Some primary deficiencies include, for example, signal drift, output offsets, gain error, limited dynamic reserve, and harmonic rejection. Additionally, external parameters such as temperature or age contribute to analog noise and, consequently, measurement uncertainty. Furthermore, analog processing is notably sensitive to component tolerances thereby limiting functional utility.

Finally, when the digital timing signals share a backplane with analog data signals, coupling can occur, causing fluctuations along the analog lines. A direct consequence of these undesirable attributes is that the instrument noise floor is elevated, causing a reduction in the detection sensitivity, diminished dynamic range for the overall system, and a slowing of the data acquisition. Analog detection systems suffer from other deficiencies and limitations, as well.

U.S. Pat. No. 7,463,362 to Lasker et al. (Lasker) discloses digital signal processor-based detection systems and methods for optical tomography to address some of the deficiencies and performance limitations of existing analog-based systems. However, there are still challenges to be addressed for digital optical tomographic imaging systems, such as system expansion (including the number of detectors), timing considerations, acquisition speed, and clinically-practical user interface design.

SUMMARY

In one aspect, the disclosed subject matter provides a method for imaging tissue using diffuse optical tomography with digital detection. The method includes directing at the tissue a plurality of amplitude modulated optical signals from a plurality of optical signal sources, illuminating the tissue at a plurality of locations; and detecting a resulting plurality of attenuated optical signals exiting the tissue to obtain a plurality of analog signals containing diffuse optical tomographic information. The method further includes converting the analog signals into digital signals and recovering the tomographic information from the digital signals using a digital signal processor-based detection module that performs digital detection. The detection module includes a master digital signal processing subsystem and at least one slave digital signal processing subsystem that processes at least a portion of the digital signals and the master digital signal processing subsystem controls the at least one slave digital signal processing subsystem. The method further includes transmitting the recovered tomographic information in digital form to a host computer for display.

In another aspect, the disclosed subject matter provides a system for imaging tissue using diffuse optical tomography with digital detection. The system includes a light delivery subsystem and a light detection subsystem. The light delivery subsystem is configured to direct at the tissue a plurality of amplitude modulated optical signals from a plurality of optical signal sources illuminating the tissue at a plurality of locations. The light detection subsystem includes at least one detector, at least one analog-to-digital converter, and a digital signal processor-based detection module. Each detector is configured to detect a resulting plurality of attenuated optical signals exiting the tissue to obtain a plurality of analog signals containing diffuse optical tomographic information. Each analog-to-digital converter is configured to convert the analog signals into digital signals. The digital signal processor-based detection module is configured to perform digital detection to recover the tomographic information from the digital signals. The digital signal processor-based detection module is also configured to transmit the recovered tomographic information in digital form to a host computer for display. The processor-based detection module includes a master digital signal processing subsystem and at least one slave digital signal processing subsystem that processes at least a portion of the digital signals. The master digital signal processing subsystem controls the at least one slave digital signal processing subsystem.

Embodiments of the disclosed subject matter may include one or more of the following features. The master digital signal processing subsystem may process a portion of the digital signals and the at least one slave digital signal processing subsystem may process a remainder of the digital signals. The at least one slave digital signal processing subsystem may process all of the digital signals. The master digital signal processing subsystem may control the at least one slave digital signal processing subsystem by providing at least one timing signal for the processing of the digital signals.

The amplitude modulated optical signals may include optical signals at a plurality of wavelengths. The optical signals may be time and frequency multiplexed. An optical signal of a first wavelength and an optical signal of a second wavelength may be amplitude-modulated at a first frequency and a second frequency, respectively, at a first time, and an optical signal of a third wavelength and an optical signal of a fourth wavelength may be amplitude-modulated at the first frequency and the second frequency, respectively, at a second time.

The master digital signal processing subsystem and at least one slave digital signal processing subsystem each may include a programmable logic device that controls processing of the digital signals. The master digital signal processing subsystem and at least one slave digital signal processing subsystem each may include a digital signal processor that controls the corresponding programmable logic device.

The analog signals may be amplified by programmable gain amplifiers controlled by the programmable logic devices. The programmable gain amplifiers may be controlled by the programmable logic device of the master digital signal processing subsystem. The programmable logic device of the master digital signal processing subsystem may supply timing signals to analog-to-digital converters that convert the plurality of analog signals into digital signals. The programmable logic device of the master digital signal processing subsystem may control the optical signal sources.

The digital detection may include multiplying the digital signals by corresponding in-phase reference signals to obtain in-phase signal components, the corresponding in-phase reference signals having the corresponding frequencies; multiplying the digital signals by corresponding quadrature reference signals to obtain quadrature signal components, the quadrature reference signal having the corresponding frequencies; passing the in-phase signal components through an averaging filter; passing the quadrature signal components through the averaging filter; computing signal amplitudes based on the filtered in-phase signal components and the filtered quadrature signal components, the signal amplitudes being representative of the tomographic information; and outputting the demodulated signal amplitudes.

The tissue may include breast tissue and a plurality of amplitude modulated optical signals may be directed at both breasts simultaneously. The tissue may include brain tissue and a plurality of amplitude modulated optical signals may be directed at both brain hemispheres simultaneously. The tissue may include extremity tissues and a plurality of amplitude modulated optical signals may be directed at both arms and/or legs simultaneously.

The plurality of amplitude modulated optical signal may be directed at the tissue and the resulting plurality of attenuated optical signals exiting the tissue may be detected while a stimulus is applied to the tissue of a patient. The stimulus may be applied by having the patient perform the Valsalva maneuver or breath pure oxygen. The stimulus may be also applied by applying a mechanical pressure to the tissue.

BRIEF DESCRIPTION OF THE DRAWINGS

The disclosed subject matter is illustrated in the figures of the accompanying drawings which are meant to be exemplary and not limiting, in which like references are intended to refer to like or corresponding parts, and in which:

FIG. 6 is a flow diagram depicting a lock in algorithm, according to one embodiment of the disclosed subject matter;

DETAILED DESCRIPTION OF THE PREFERRED EMBODIMENTS

In the following description of the preferred embodiments, reference is made to the accompanying drawings that form a part hereof, and in which is shown by way of illustration a specific embodiment in which the disclosed subject matter may be practiced. It is to be understood that other embodiments may be utilized and structural changes may be made without departing from the scope of the present disclosed subject matter.

To make quantifications of biological or physiological processes, a transducer is generally required to convert modified parameters into a detectable measurement. In some cases, the modified parameter is photon flux. For example, a light source may be directed at a specific tissue or limb of interest and the attenuated light exiting the tissue is detected at multiple positions along the surface. These measurements are then fed through an image reconstruction algorithm whose results impart insight into anatomic structure or physiologic conditions. Imaging with multiple wavelengths allows one to perform spectral analysis and quantify changes in hemoglobin parameters such as oxy and deoxy-hemoglobin, or other biological chromophores.

Figure 1:
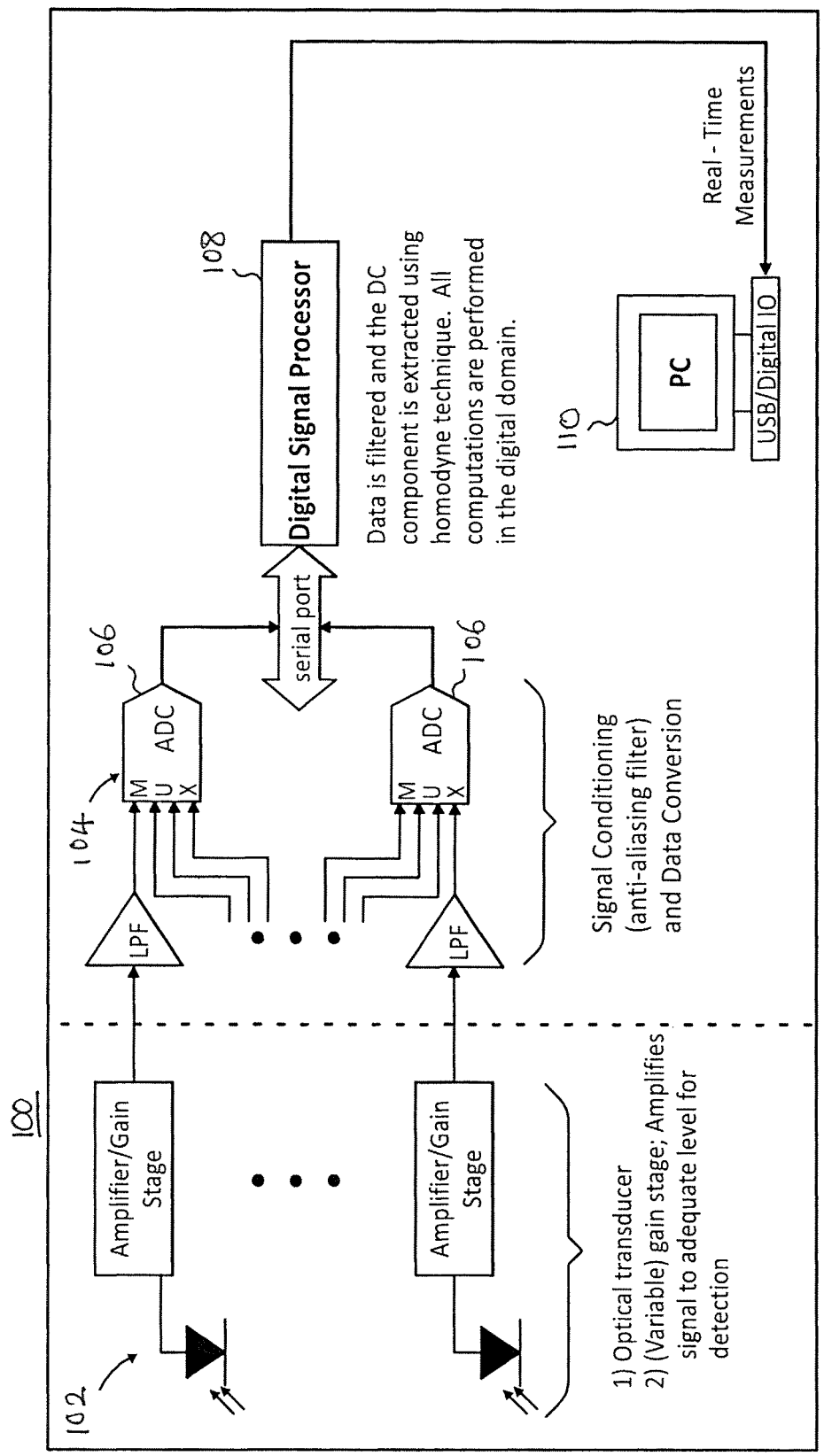
FIG. 1 is a block diagram of an optical tomography system that uses digital detection, according to one embodiment of the disclosed subject matter.

FIG. 1 is a block diagram of an optical tomography system 100 (a system used in or for optical tomography, or aspects thereof) that uses digital detection, as discussed in Lasker. As depicted in FIG. 1, instead of performing further analog conditioning, as in some previous systems, the modulated signal is digitized immediately following programmable gain segment 102. As generally required for a digital conversion process, an anti-aliasing filter is included, and is depicted as included in segment 104. ADC 106 samples the analog channels two at a time. Data samples get clocked out of the ADC 106 and into the DSP 108 via a serial port connection. Once in the DSP 108, it goes through a digital lock-in filter which also consists of a mixing process and low-pass filter. Upon completion of all computations, the DSP 108 sends out the data to the host PC 110 for storage, display, and image reconstruction.

Compared to previous systems, the disclosed embodiments achieve many improvements in performance. The electrical noise on each channel is decreased. This noise consists of two components: one is the intrinsic noise generated by the electronics themselves and the other is extrinsic noise, radiated from some outside source. The settling time of each channel after a change in source positions is decreased, thereby increasing the temporal resolution. This settling time is the limiting factor determining overall image frame rate.

The size of the system is decreased. For example, an instrument according to some embodiments of the disclosed subject matter can have one analog detection channel per circuit board using through-hole components. By using surface-mount components, four or eight analog channels per board can be used, decreasing the number of total boards.

The input dynamic range of the system is increased. Also, the overall power consumption of the analog detector boards is decreased by reducing the power supplies from +/−18V to +/−5V. This may help prevent board heating and reduce drift due to temperature changes.

Another advantage of the disclosed embodiments is that digital filtering is utilized to process incoming data and to perform the homodyne detection. In certain embodiments, the instrument is designed to accommodate up to four modulation frequencies. Adding more wavelengths is possible, and some embodiments of the disclosed subject matter use additional frequencies. The software lock-in amplifier dictates constraints on the modulation frequencies and the number of samples to be acquired. Therefore, defining a modulation bandwidth in the range from 3 kHz to 9 kHz allows some flexibility in choosing modulation frequencies and the number of samples. This range may be determined based at least in part upon the specifications of other system components, such as the bandwidth of the transimpedance amplifiers. Wider ranges may be used with appropriate changes to the specifications of these components.

Figure 2:
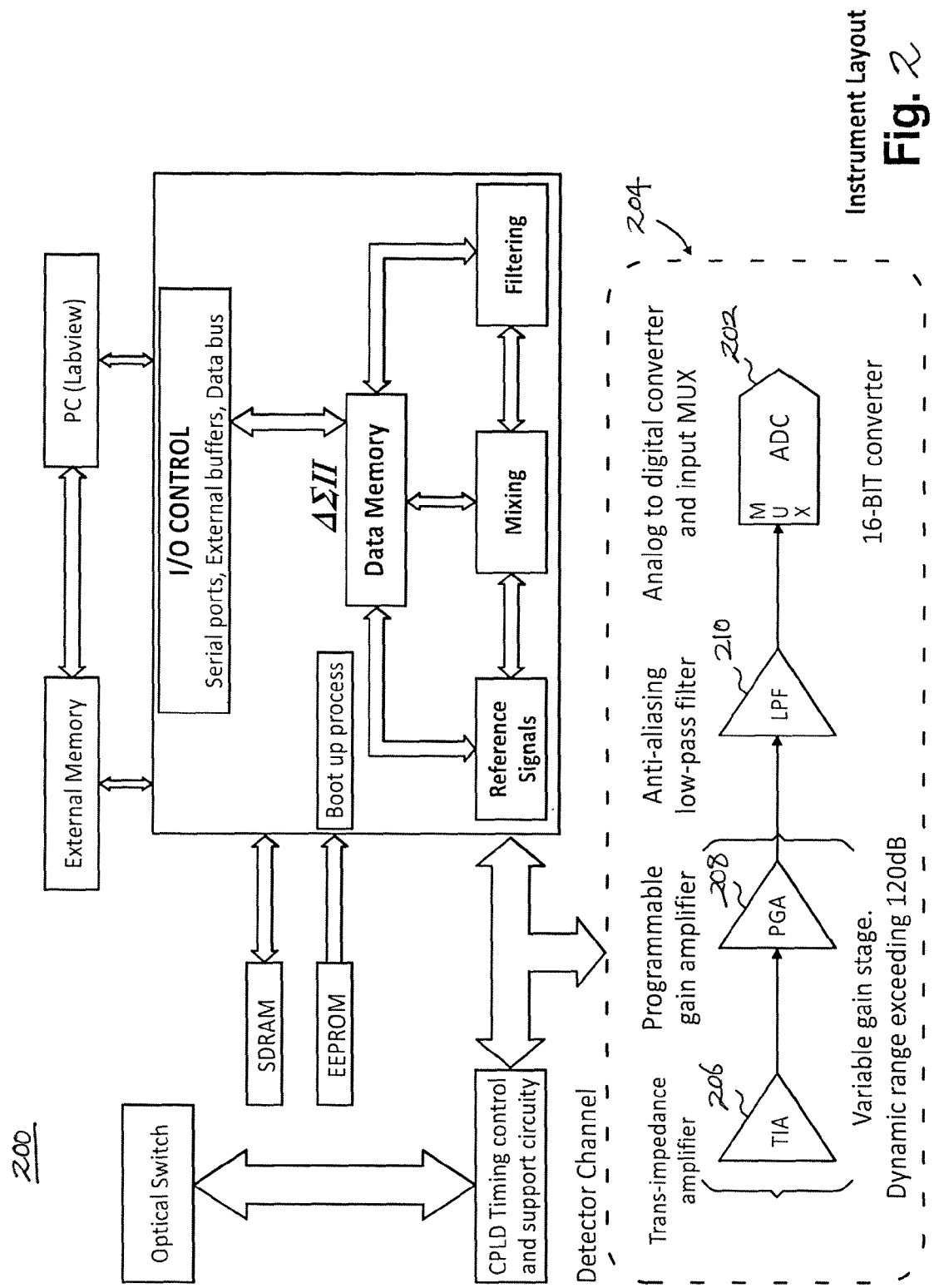
FIG. 2 is a block diagram of an instrument layout for an optical tomography system that uses digital detection, according to one embodiment of the disclosed subject matter.

FIG. 2 is a block diagram of an instrument layout for an optical tomography system 200 that uses digital detection. The analog-to-digital converter (ADC) function is implemented in the analog detector boards, such as ADC 202 of detector channel 204, as depicted in FIG. 2. Each ADC has an internal 4-channel MUX, so that four detector channels can be included on each detector board. Each detector channel will consist of a trans-impedance amplifier (TIA), a programmable-gain amplifier (PGA), a low-pass filter (LPF), and the ADC 202. For example, as depicted in FIG. 2, the detector channel 204 includes TIA 206, PGA 208, LPF 210, and the ADC 202.

Figure 3:
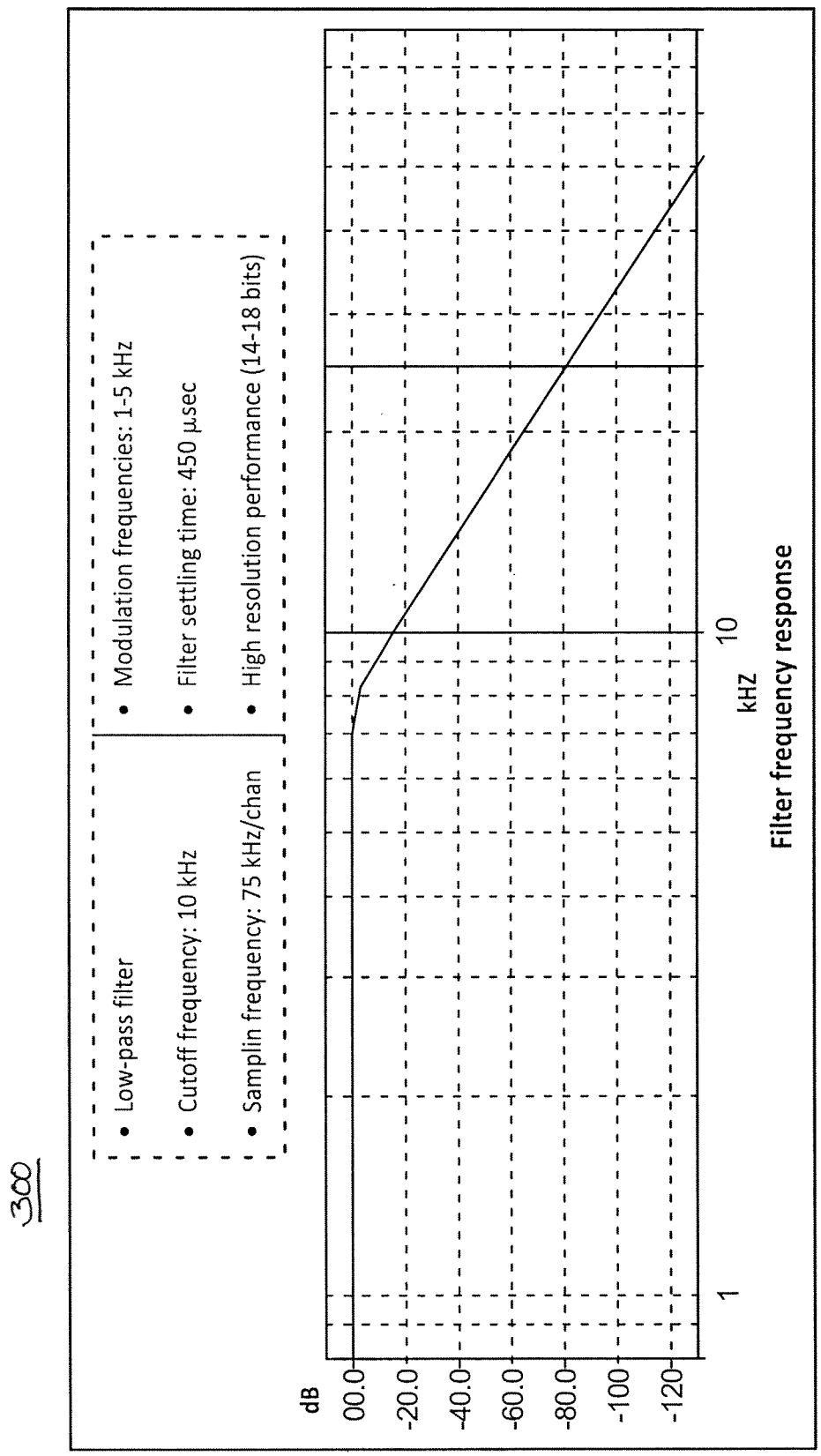
FIG. 3 is a graph depicting filter frequency response of an anti-aliasing filter, according to one embodiment of the disclosed subject matter.

FIG. 3 is a graph 300 depicting filter frequency response of a low pass anti-aliasing filter according to one embodiment of the disclosed subject matter. In previous systems, analog signals were passed through a backplane and eventually to an ADC card on a host PC. By putting an ADC on each analog detector board, as is done according in some embodiments of the disclosed subject matter, the amount of noise picked up between the Analog Detection Boards (ADB) and the host PC is reduced (digital data transmission has much better noise immunity). This helps to decrease the extrinsic noise on each channel.

The lock-in amplification (LIA) function is performed in software, and one benefit of this is a decrease in the settling time of the detector electronics. Preliminary LIA code shows settling times in the 1-2 ms range, as opposed to typically 7 ms in a hardware LIA. The rest of the electronics in the digital detector board may take from 2-4 ms to settle (determined by the high-pass filter at the TIA output—this can probably settle simultaneously with the source switch). The overall settling time of the system's detector electronics according to some embodiments of the disclosed subject matter (not including the source switch) is between 3 ms and 6 ms (easily adjustable within this range by minor differences in the design).

Another benefit to having the LIA in software, as is done in some embodiments, is a decrease in the complexity of the ADB. Furthermore, significant performance benefits can be realized by implementing the LIA in the digital domain. This is a result of eliminating the adverse analog effects of the analog electronics, analog signal processing, and filter chips—and being able to customize the filter for user-specific applications. To increase the system's input dynamic range, according to some embodiments of the disclosed subject matter, a third gain setting for the TIA is included. This 1-kΩ gain setting will be included with the previous 10-kΩ and 10-MΩ gain settings. In some embodiments, a fourth gain setting of 100-MΩ is also available.

The following is a description of aspects of a TIA according to some embodiments of the disclosed subject matter, such as the TIA 206 depicted in FIG. 2, as referenced above.

In systems according embodiments of the disclosed subject matter, such as the system 200 depicted in FIG. 2, there may be three or more values of TIA Rf to choose from (e.g., 1 kΩ, 10 kΩ and 10 MΩ). The PGA 208 of system 200 has, for example, three gain settings (e.g., 1, 10 and 100). This allows for overall gains ranging from 1 kA/V to 1 G\A/V spaced by a factor of 10. Using the 1 kΩ resistor results in a 10 times larger input dynamic range at the lowest gain setting. One motivation for this gain flexibility is the realization that when performing measurements on small geometries (1 cm-3 cm), as is common with small animal imaging, the TIA stage will readily saturate for small optode separations and intensity filters must be introduced. Increasing the dynamic range of the TIA 206 through this 1 kΩ resistor helps eliminate the need for optical filters, thereby making the instrument suitable for imaging small animals as well as large tissue structure.

For the TIA 206 depicted in FIG. 2, in order to achieve three TIA gain settings, two reed relays ($K_1$ and $K_2$) can be used to switch the three feedback resistors ($R_1$, $R_2$ and $R_3$). These reed relays can be controlled by an 8-1 analog MUX and three gain bits. When one of the MUX's analog inputs is selected, the corresponding reed relay coil is grounded through the MUX. This allows the relay coil to conduct, closing the switch. When $K_1$ or $K_2$ is activated, $R_1$ or $R_2$ is placed in parallel with $R_3$. Since $R_1$ and $R_2$ are both at least 1000 times lower than $R_3$, it follows that $R_1$ or $R_2$ sets the gain of the TIA when $K_1$ or $K_2$ is activated. In some embodiments, only one reed relay switch can be closed at a time (because only one channel of the 8-1 MUX can be selected at a time). In some embodiments, since the reed relays consume more current than any other circuit element, it is significant that only one can be activated at a given time. When neither of the relays is closed, $R_3$ sets the TIA gain.

For the TIA 206 depicted in FIG. 2, the TIA circuit consists of an op-amp, two reed relays, a MUX, and various passive components. The following includes an explanation of component selections. In some embodiments of the disclosed subject matter, a photodiode such as that used and described in Schmitz 2002 is utilized.

For the TIA 206 as depicted in FIG. 2, the op-amp ($IC_1$) utilized has a very low input bias current. This is important when trying to accurately measure photodiode currents in the tens of picoamps range. The op-amp also has low voltage noise and low current noise. With a 10 MΩ feedback resistor, this current noise generates a voltage noise of 7 uV. This is less than the resistive thermal noise of the 10 MΩ resistor. It is believed that the current noise increases with temperature, so it is important to keep the temperature not much higher than 25° C.

The following is a description of a PGA that can be utilized in embodiments of the disclosed subject matter, such as the PGA 208 as depicted in FIG. 2.

As mentioned in the TIA discussion, PGA gains of 1, 10 and 100 can be used. To implement the PGA 208, an instrumentation amplifier (gain programmed by a resistor) is used; an 8-1 MUX; and various passive components.

For the PGA 208, to change the PGA gain, the 8-1 MUX connects a different resistor between pins 1 and 8 of the instrumentation amplifier based on two control bits. The particular in-amp used for the PGA 208 is available from Texas Instruments, Inc., although other in-amps may be utilized in other embodiments of the disclosed subject matter. This amplifier has low quiescent current, low input bias current, low input offset voltage, low non-linearity, dual supply operation and a high gain-bandwidth product.

The Analog Devices Model ADG608B MUX, available from Analog Devices, Inc., can be used as the analog MUX because it operates on ±5-V supplies and has an acceptable on-resistance (measured to be about 16Ω). Operating on ±5-V supplies is important because the input can be positive or negative.

Resistors, according to some embodiments of the disclosed subject matter, can be chosen for PGA gains of 1, 10 and 100 according to Equation (1):

$$G = 1 + \frac{50 \text{ k}\Omega}{R + 16 \text{ }\Omega} \tag{1}$$

The addition of 16Ω in the denominator of Equation (1) is due to the on resistance of the MUX.

To change the PGA gain, the 8-1 MUX—governed by two control bits—connects a different resistor $R_G$ across the appropriate pins of the instrumentation amplifier. The following chart (Table 1) tabulates the total effective signal gain based on the values of all three control bits.

TABLE 1

| G2 | G1 | G0 | TIA gain (Ω) | PGA gain (V/V) | Overall Gain (Ω) |
|----|----|----|--------------|----------------|------------------|
| 0  | 0  | 0  | 1k           | 1              | 1k               |
| 0  | 0  | 1  | 10k          | 1              | 10k              |
| 0  | 1  | 0  | 10k          | 10             | 100k             |
| 0  | 1  | 1  | 10k          | 100            | 1 M              |
| 1  | 0  | 0  | 10 M         | 1              | 10 M             |
| 1  | 0  | 1  | 10 M         | 1              | 10 M             |
| 1  | 1  | 0  | 10 M         | 10             | 100 M            |
| 1  | 1  | 1  | 10 M         | 100            | 1 G              |

In some embodiments, the appropriate gain values are determined prior to making a measurement and depend on the target geometry, tissue density, and the detector's proximity to the light source. These values for all detector channels must be updated for each source position. The corresponding bits can be stored in local memory banks located on each detector card and made available for immediate access. Including the on-board memory cache into the modular structure of the detector cards has numerous advantages. First, it eliminates the need for a designated gainbit-routing board. Because of the substantial fan-out generated by such a routing board, it necessitates a sizable allotment of space and produces many parallel lines running throughout the instrument. Secondly, this modular format makes it very simple to add additional detector channels without requiring a system restructure. Furthermore, it is a compact and efficient way of distributing the gainbit values.

The following description relates to aspects and specifications of an anti-aliasing LPF according to embodiments of the disclosed subject matter, such as the LPF 210 depicted in FIG. 2.

In some embodiments, the system 200 is designed to provide a signal passband from 3 kHz to 9 kHz (with 1% flatness). Since the TIA 206 sets the attenuation at 9 kHz to 1%, the attenuation at 9 kHz caused by the LPF stage is to be minimized. In some embodiments, the system 200 is designed to provide a 0.1% LPF attenuation at 9-kHz and as steep of a roll-off as possible after 9 kHz while preserving flatness in the passband. This roll-off attenuates any noise above 9 kHz, aiding the LPF function implemented in the LIA. It also provides anti-aliasing before sampling of the signal with the ADC. Since the noise floor for an ideal 16-bit ADC is −96 dB, the system 200 is designed to provide at least this much attenuation at any frequencies that could alias to 9 kHz or below. The LPF 210 is designed to have a good time response to a step input (for when the source position and gain settings switch) and to settle to 16-bit accuracy in less than 1 ms with a full-scale step input. Also, the LPF 210 IC is designed to provide low-power and small size.

In some embodiments, the LPF 210 is implemented with an $8^{th}$ order Butterworth filter. The Butterworth filter topology tends to have a flat passband and relatively steep roll-off. It also tends to have a good time response to step inputs. An $8^{th}$ order filter can be used because it is practical with the currently available filter ICs. Higher orders would require more filter ICs in series (increasing size and power consumption), while lower orders do not provide the necessary attenuation at frequencies just above 9 kHz. A cutoff frequency of 12.5 kHz is used to meet the specification of 0.1% LPF attenuation at 9 kHz. Assuming a sampling frequency of 75 ksps, noise appearing in the 67 kHz-72 kHz and could alias into the passband. However, this LPF more than adequately performs its antialiasing function (−117 dB attenuation at 67 kHz).

In some embodiments, the system 200 utilizes two 4th order filter ICs, cascaded to implement the $8^{th}$ order Butterworth LPF. These filter ICs have low noise and distortion (specified for 16-bit systems). They are continuous-time active filters so they do not suffer from clock noise as switched-capacitor filters do. In some embodiments, these $4^{th}$ order filter Ics are used instead of a single $8^{th}$ order IC because these have a low-power mode with a quiescent current of 2.2 mA each. This is considerably less current consumption than the lowest single-IC $8^{th}$ order continuous-time filters.

The following description relates to aspects and specifications of an ADC buffer according to embodiments of the disclosed subject matter.

In some embodiments, the system 200 incorporates a 2.5V offset into the input buffer of the ADC 202. Signals exiting the LPF 210 are centered about zero volts whose amplitude has an upper limit of $5V_{p-p}$. The ADC though, operates between 0V and +5V so we must add a 2.5V offset to form a pseudo-bipolar signal. This preserves the $5V_{p-p}$ now centered around 2.5 volts. The driver must be able to settle for a full-scale step of the capacitor array at a 16-bit level (0.0015%). Furthermore, the noise generated by the driver must be kept to a minimum in order to preserve the SNR performance of the ADC.

The following description relates to aspects and specifications of a DSP according to embodiments of the disclosed subject matter, such as the DSP 108 depicted in FIG. 1, as referenced above.

In some embodiments, the system 200 is designed to provide the highest possible resolution ADC while retaining the ability to sample at ≤50 ksps for each of four multiplexed channels. In some embodiments, the ADC 202 can have at least a four-channel input multiplexer built-in. It can also have a serial output to the DSP 108. This will result in less digital data lines than a parallel data output. Low current consumption would also be helpful, but is not critical since there is only one ADC 202 per four detector channels in this embodiment.

In some embodiments, with respect to the ADC utilized, such as the ADC 202 depicted in FIG. 2, a 4-channel, 16-bit, 1 Msps ADC, is used. The effective number of bits of this ADC is about 14. This is sufficient because the noise floor of the analog electronics may not permit better than 14-bit resolution except for two gain settings (noise is dominated in most gain settings by the TIA feedback resistor). The 1 Msps sampling rate allows sampling of each channel at a sufficiently high rate (sampling is being done at ~75-80 ksps). It also has a relatively low current consumption.

The ADC's can sample two channels simultaneously. Initially it samples the first two channels, whose samples are read into the DSP 108 over the serial port line. The MUX is then switched and it samples and clocks out the remaining two channels.

The following includes a description of aspects and functions of a DSP and a complex programmable logic device (CPLD), according to some embodiments of the disclosed subject matter. It is through these devices where the multitude of tasks takes place for each source position and each imaging frame.

In some embodiments of the disclosed subject matter, the Digital Signal Processor (DSP) plays a substantial role in data acquisition timing and overall system control, providing or helping to provide a number of advantages to an instrument into which it is integrated, which can include computational power, flexibility, and speed.

In some embodiments, upon power up, the DSP goes through a boot-up sequence which loads the programming code into internal memory. This sequence is a set of instruction used to initialize and direct the loading of the DSP. This boot-sequence is stored in an on-board EEPROM and the DSP is programmed to download and read its contents when power is applied.

In some embodiments, the DSP goes through a series of system initialization processes so that registers are appropriately prepared for running experiments. These processes include:
1) Initialize CPLD;
2) Setup interrupt vector table;
3) Initialize programmable digital I/O lines;
4) Clear serial port registers;
5) Program serial port registers;
6) Program gain-bit DMA (Direct Memory Access);
7) Setup imaging DMA;
8) Setup timer;
9) Setup external port buffer;
10) Generate reference signals (for each wavelength); and
11) Go into standby.

In standby, the DSP is continuously polling the digital I/O fines connected to the PC waiting for an instruction. In some embodiments, there are three possible instructions.

A) Download Gain-bit values;
B) Start Imaging;
C) Stop Imaging;

In some embodiments, with respect to (A) Download Gain bit values, as mentioned above, the following operations are carried out for each request:

a. Gain-bit values are received from the PC, sent over the data bus through a relevant transfer protocol, and stored in DSP onboard memory.

b. DSP sends instruction word to CPLD and tells it to begin going through gain-upload sequence.

c. The gainbits for all channels are sent out from the DSP one source at a time and are routed to the detector boards by the CPLD. The DSP increments through the number of sources and then stops when all bits are uploaded. The gainbits are sent out over the serial port transmit line using a DMA protocol which has an independent processor so the DSP's core is not occupied with I/O responsibilities.

In some embodiments, with respect to (B) Start imaging, as mentioned above, the following operations are carried out for each request:

a. Send instruction word to CPLD over serial line and tell it to begin imaging process.

b. Initialize timer that counts 5 msec for the electronics and light source to settle.

c. Setup serial-port receive-DMA which is used to receive the digitized samples for all detector channels.

d. Wait for timer interrupt. Disable timer. CPLD controls sampling process and DSP waits for the data to come in over the serial port. Data coming into the DSP is time-division-multiplexed. The DMA channel is setup such that it collates the samples for each channel so that when sampling is complete, data is organized in the DSP's memory block.

e. When all data is received, another interrupt is generated that starts the lock-in algorithm. The DSP mixes the reference signals and the data samples. It filters the resulting signal with an averaging filter (more detail on that below) to discard the higher frequency components.

f. When processing is complete, data is sent to external memory via the data bus where it is streamlined into the host PC by either a Universal Serial Bus (USB) controller or a digital I/O board. This too is sent out through means of a DMA procedure.

g. Steps b-f are repeated for all sources until the imaging frame is complete. After data from last source is received, the DSP check the digital I/O status line to see if it should image another frame.

In some embodiments, with respect to (C) Stop imaging, as mentioned above, the following operations are carried out for each request:

a. If control lines indicate termination of data acquisition, the DSP completes the frame it is processing and then stops. The CPLD does the same.

b. Return to standby.

In systems according to some embodiments of the disclosed subject matter, the CPLD acts as a multi-level state machine and can execute a variety of standard logic operations. Once enabled, the CPLD's main state machine enters standby mode. There it waits for an instruction from the DSP telling it to enter either the Gainbit or Imaging state-machines.

In some embodiments, after entering a Gainbit state machine, the CPLD performs the following:

a. Initialize FIFOs and shift registers.

b. Get number of sources for experiment from DSP.

c. Receive gainbit data from DSP and clocks them through the shift registers on the detection boards. When gain upload is complete, the CPLD writes them into their respective FIFOs where they are stored and used during the imaging routine. This procedure is executed successively, one source at a time for all activated sources positions.

d. Returns to standby in main state-machine.

In some embodiments, after entering a Gainbit state machine, the CPLD performs the following:

a. Move source switch into position.

b. Wait for settling time trigger from DSP.

c. Begin conversion/sampling sequence. Signals are sampled half the channels at a time being that each ADC sample two channels simultaneously. Digitized data is time-division multiplexed onto the DSP's serial port. As these samples are clocked into the DSP, the CPLD is updating the address of the ADC's MUX. The next conversion signal read by the ADCs are used for the remaining channels. When all samples for all channels have been taken, the CPLD repeats steps a-c until imaging frame finishes in its entirety.

d. Goes into standby waits for another imaging instruction.

Figure 4:
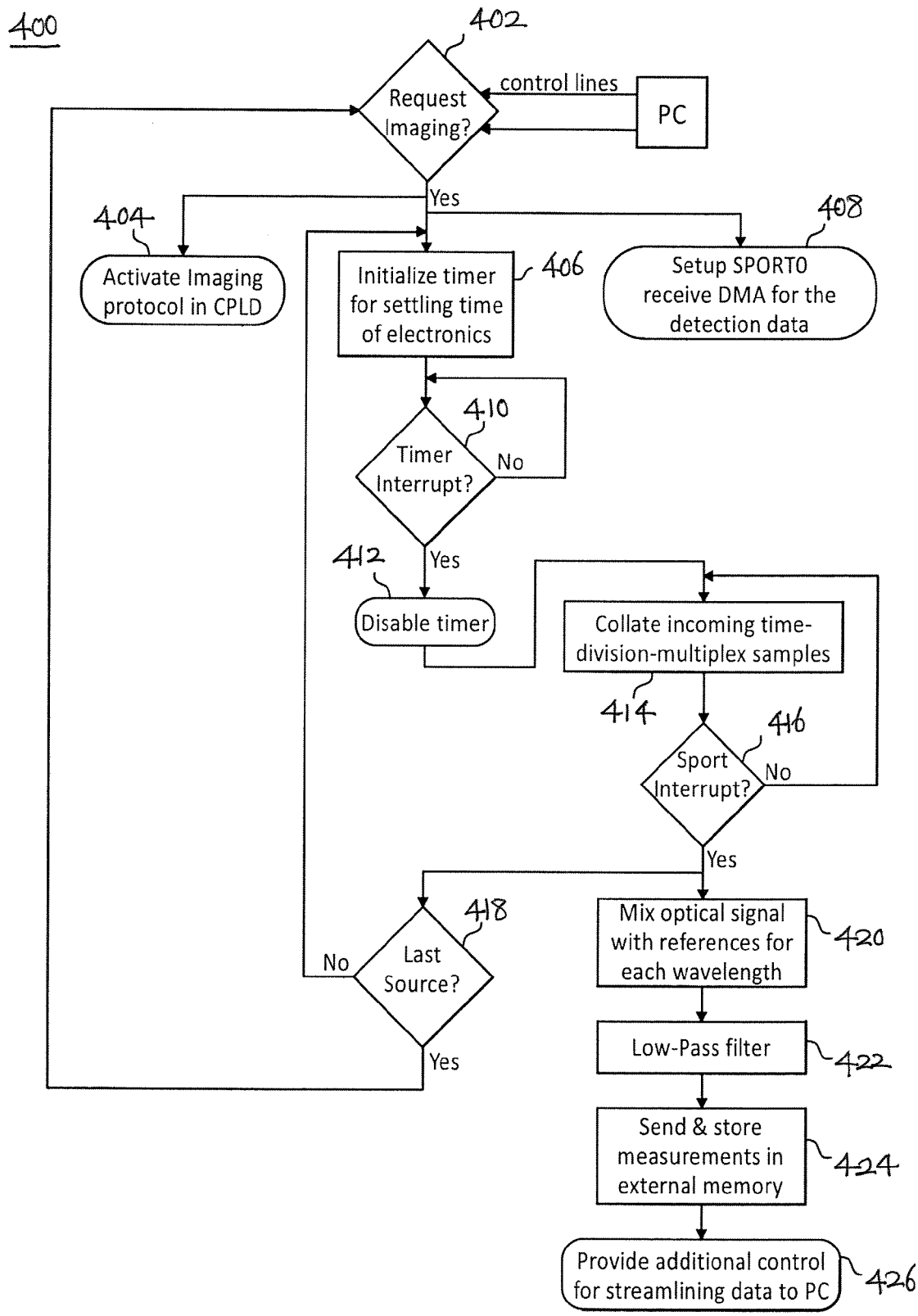
FIG. 4 is a flow diagram depicting a digital signal processor-based Imaging routine, according to one embodiment of the disclosed subject matter.

FIG. 4 is a flow diagram depicting a DSP-based Imaging routine 400, according to one embodiment of the disclosed subject matter. At step 402, it is inquired whether an imaging request has been issued.

If an imaging request has been made, the routine 400 proceeds to steps 404, 406, and 408. These steps include, respectively, activate imaging protocol in the CPLD, initialize timer for settling time of electronics, and setup SPORT (Serial Port) receive DMA for the detection data.

Following step 406, the routine 400 proceeds to step 410, at which it is queried whether a timer interrupt has been issued. If not, then the routine 400 remains in query step 410.

If a time interrupt has been issued, the routine 400 proceeds to steps 412 and 414, at which include, respectively, disable timer and collate incoming time-division multiplex samples.

Following step 414, the routine 400 proceeds to step 416, at which it is queried whether a SPORT interrupt has been issued. If not, then the routine remains at step 414.

If a SPORT interrupt has been issued, the routine 400 proceeds to step 420, which includes, mix optical signals with references for each wavelength.

Following step 420, the routine 400 proceeds to step 422, which includes utilization of the LPF, and also returns to step 418.

At step 418, it is inquired whether the source is the last source. If yes, then the routine 400 returns to step 402. If no, then the routine 400 returns to step 406.

At step 422, the low pass filter is utilized. Following step 422, the routine 400 proceeds to step 424, which includes sending & storing measurements in external memory.

Following step 424, the routine 400 proceeds to step 426, which includes providing additional control for streamlining data to a computer or computerized device, such as a personal computer (PC), or, in some embodiments, over one or more networks to one or more computing devices. Herein, wherever a PC is depicted or described, it is to be understood that the PC could be any computing device or devices, and could be reachable through or include one or more networks.

Figure 5A:
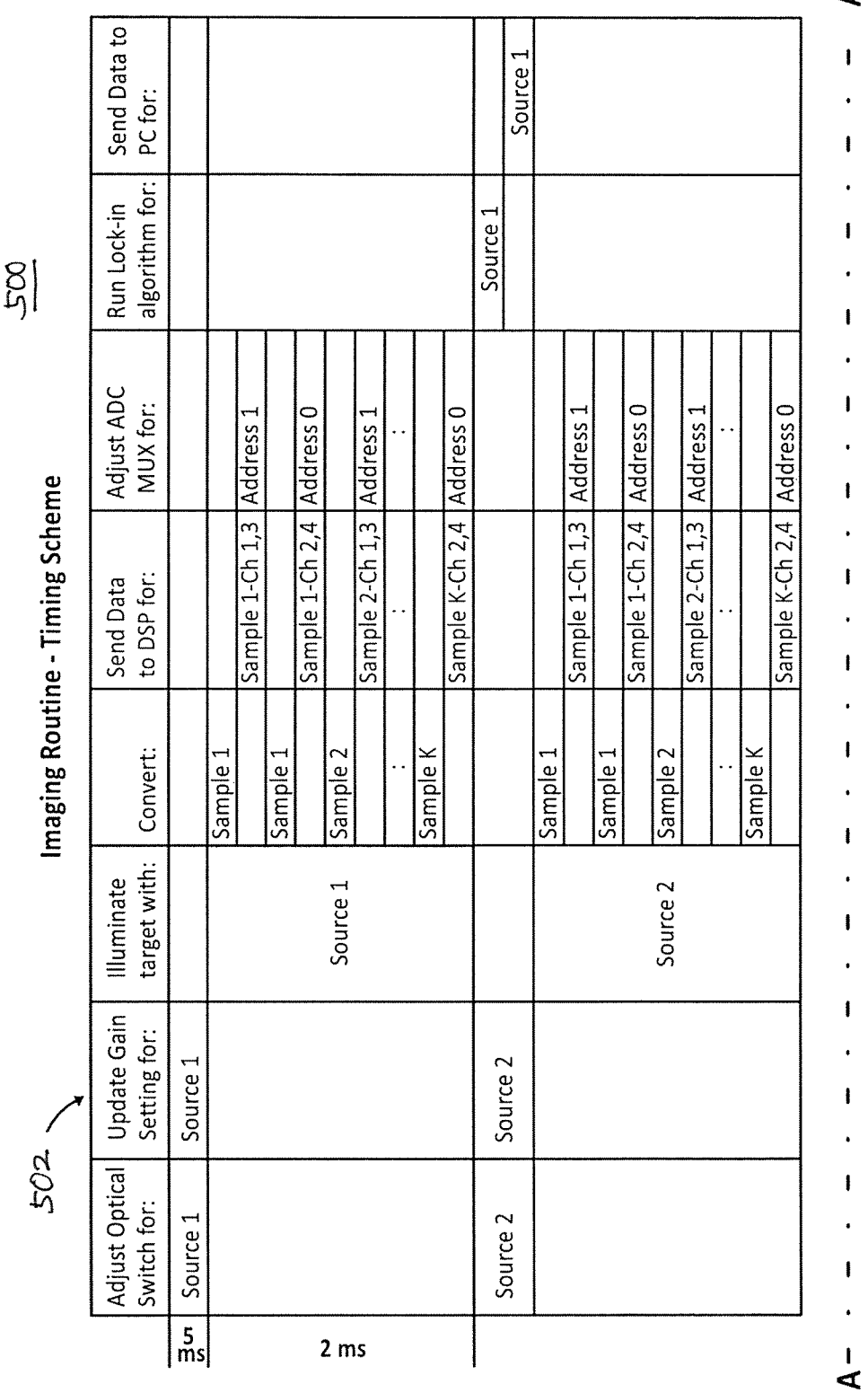
FIGS. 5A and 5B are a table depicting a timing scheme for an imaging routine, according to one embodiment of the disclosed subject matter.
Figure 5B:
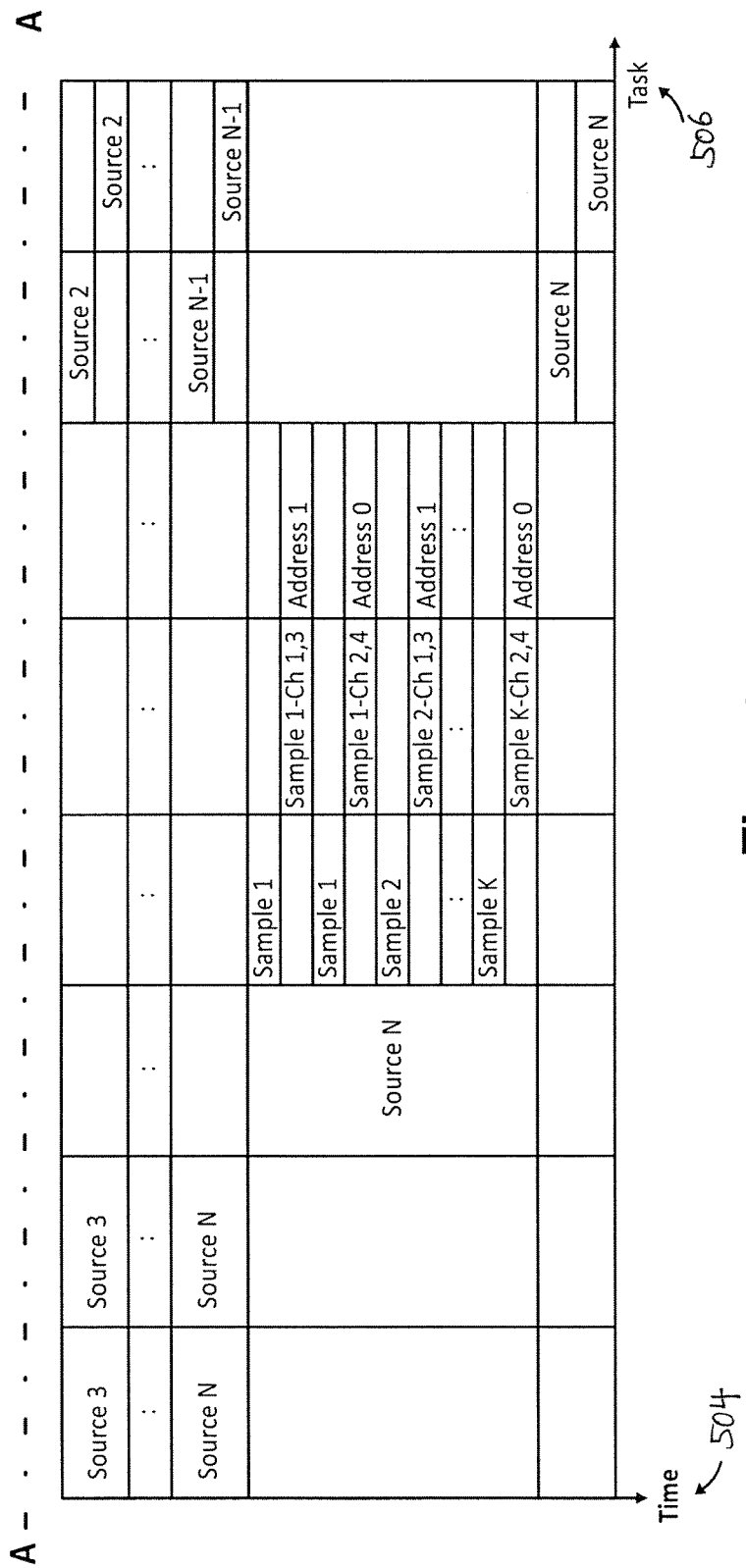

FIGS. 5A and 5B are a table depicting a timing scheme 500 for an imaging routine, according to one embodiment of the disclosed subject matter. As depicted, the vertical axis 502 indicates time passing as the axis 502 proceeds downwardly, while each task 506 is indicated by an entry in the table 502 in a vertical position indicating the time or time period at which the task is performed or accomplished.

FIG. 6 is a flow diagram depicting one type of lock in algorithm 600, according to one embodiment of the disclosed subject matter.

At step 602, according to the algorithm 600, a digital lock-in filter is used with the following constraints, the filter being ideal for discrimination of frequency encoded sources (different wavelength λ.):

$$f_{\lambda,i} = m_i(f_s/K),\quad (2)$$

where:
- $f_{\lambda,i}$=Modulation frequency for source I;
- $f_s$=ADC sampling frequency;
- K=Number of samples per source;
- $m_i$=positive integer for source i $1<m_i<K/2$; and $$\text{Filter Settling time } T_F = K/f_s,\quad (3)$$

where:
- use $f_s$=75 KHz, K=150 samples; and
- $f_{\lambda,i}=m_i*(0.5)$ KHz, $T_F$=2 ms At step 604, the algorithm 600 extracts from the measured signal M[k] the amplitude $A_{\lambda,i}$ of the component due to wavelength λi.

At step 606, the algorithm stores K values for cosine (In-phase) and sine (Quadrature) wave at frequencies $f_{\lambda,i}$.

At step 608, M[k] is modulated by the stored signals forming quadrature components and then passed through an averaging filter in accordance with the following equations:

$$I_{\lambda i} = \frac{1}{K}\sum_{k=1}^{K}\left(M[k]\cos\left[2\pi\frac{f_\mu}{f_s}k\right]\right),\quad (4a)$$

$$Q_{\lambda i} = \frac{1}{K}\sum_{k=1}^{K}\left(M[k]\sin\left[2\pi\frac{f_\mu}{f_s}k\right]\right),$$

At step 610, the quadrature rule is finalized to produce phase-shift independent amplitude, in accordance with the following equation:

$$A_{\lambda,i} = 2\sqrt{I_{\lambda,i}^2 + Q_{\lambda,i}^2}.\quad (4b)$$

Figure 7:
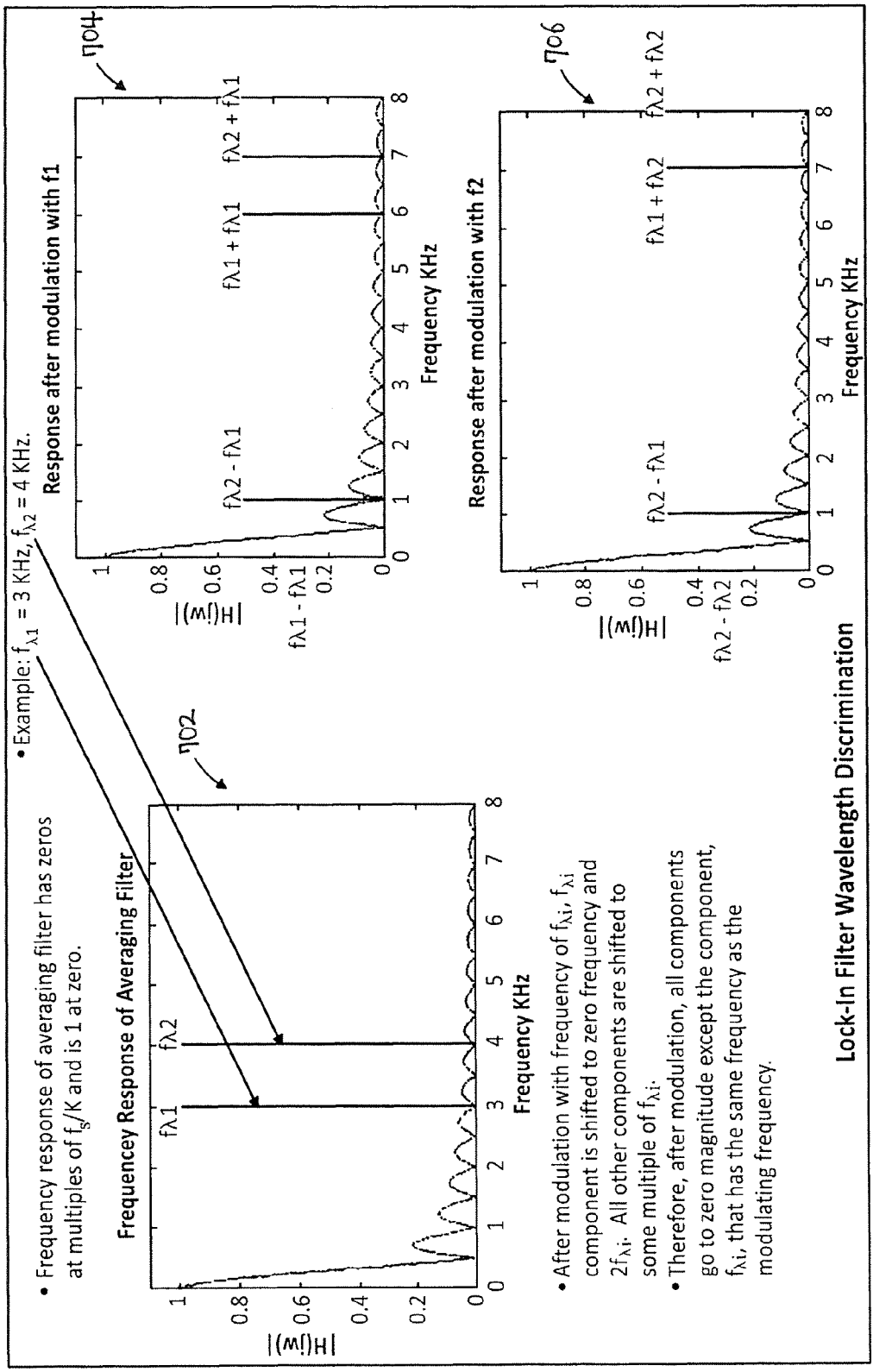
FIG. 7 is a set of graphs depicting lock-in filter wavelength discrimination, according to one embodiment of the disclosed subject matter.

FIG. 7 is a set of graphs 702, 704, 706 depicting lock-in filter wavelength discrimination, according to one embodiment of the disclosed subject matter.

It is to be noted that, in some embodiments, the lock in filter can be, but is not limited to, an ordinary averaging filter.

The averaging or mean filter is presented and described in detail such that its unique exploitation, according to some embodiments of the disclosed subject matter, is demonstrated. However, other digital filters, including but not limited to, cascaded RC filters, Bessel filters, critically damped filters etc., are utilized in some embodiments of the disclosed subject matter.

Other digital low-pass filter characteristics include, but are not limited to, Bessel and critically damped (CD) filters. Both are characterized by a good time-domain response, i.e. fast settling and little overshoot and ringing. A multi-order CD filter is used in some embodiments of the disclosed subject matter because it has superior step response characteristics (i.e. fast settling without overshoot) compared to other filter types. The CD filters' disadvantage of a slow roll off—a severe limitation of their use in analog implementations—is overcome, in some embodiments, by numerically cascading multiple filter stages. For example, a 20th-order CD filter has comparable roll-off characteristics to a 4th-order Butterworth at far superior settling characteristics (D. G. Robertson, J. J. Dowling, "Design and responses of Butterworth and critically damped digital filters," J Electromyogr Kinesiol. 2003 December; 13(6):569-73).

The following provides a brief mathematical synopsis of the lock-in algorithm 700, as referenced above, and is followed by a unique exploitation of a simple finite impulse response (FIR) low pass filter, according to one embodiment of the disclosed subject matter.

One stipulation imposed on by phase sensitive detection is that the source intensity must be modulated with a sinusoidal waveform. In our instance, this is accomplished by modulating the bias current feeding the laser diode. Say that our input signal for channel j is expressed as $V_{mj}(t)=A_{mj}\cdot\sin(2\pi f_m t+\phi_{mj})$, where $A_{mj}$ is the amplitude of the optical signal at detector j, $f_m$ is the source (modulation) frequency, and $\phi_{mj}$ is the phase shift. Since we are digitizing this waveform by acquiring $N_s$ samples at frequency $f_s$ hertz (sampling rate), it retains a discretized representation of $V_{mj}[n]=A_{mj}\cdot\sin(2\pi f_m n/f_s+\Phi_{mj})$. Now suppose we have a digitally synthesized reference signal whose format is also an Ns point discrete sequence and is represented by $S_{ref}[n]=A_r\cdot\sin(2\pi F_r n/r_s+\Phi_{ref})$ where $A_r$ is the amplitude of the reference signal, $F_r$ is the reference frequency, and $\phi_{ref}$ is its respective phase shift. If these two signals are multiplied together, the product consists of multiple elements:

$$V_{mj}\cdot S_{ref}=A_{mj}A_r(1/2)\{\cos([2\pi f_m-2\pi f_r](n/f_s)+\Phi_{mj}-\Phi_{ref})-\cos([2\pi f_m+2\pi f_r](n/f_s)+\Phi_{mj}+\Phi_{ref})\}\quad (5)$$

{using the trigonometric identity; sin u sin v=(1/2){[cos (u−v)−cos(u+v)]}

Homodyne (synchronous) detection dictates that the reference frequency must be identical to the source-modulation frequency. Applying this constraint to the above equation yields;

$$I_{mj}[n]=V_{mj}\cdot S_{ref}=A_{mj}A_r(1/2)\{\cos(\phi_{mj}-\phi_{ref})-\cos([4\pi f_m(n/f_s)]+\Phi_{mj}+\Phi_{ref})\}\quad (6)$$

The two components provide unique frequency contributions to the composite waveform; one is sitting at zero frequency (DC) whose magnitude is proportional to the phase difference between the optical and reference signals, and another component that is positioned at twice the modulation frequency on the Fourier spectrum. By sending the resulting signal through a low-pass filter we suppress the higher frequency component to obtain:

$$X_{mj}[n]=A_{mj}A_r(1/2)\{\cos(\phi_{mj}-\phi_{ref})\}=A_{mj}A_r(1/2)\{\cos(\theta_j)\}\quad (7)$$

The amplitude of the output signal is contingent on the amplitudes of the detected signal, the references signal, and the phase difference between them. If a fixed phase relationship is maintained and doesn't vary over time, then the final DC signal is directly proportional to the input signal. In an effort to maximize the DC value, one would normally be required to incorporate various phase shifting schemes. This problem is compounded in our application because each channel retains a distinctive phase, a consequence of the sampling process. Therefore, employing independent phase shifters would be imposed on the system for each detector channel and each wavelength. In some embodiments, to avoid the complexity of having to integrate many individual phase shifters, a solution is provided that makes use of an additional mixing stage with a quadrature reference signal.

The quadrature lock-in method is an elegant approach with which one can eliminate the phase dependency entirely. To accomplish this, the input signal must also be multiplied by a 90-degree phase-shift of the original reference, $C_{ref}[n]=A_r\cdot\sin(2\pi f_r n/f+\Phi_{ref}+\pi/2)$. Similar to the procedure outlined above, when the two signals are mixed and passed through a low-pass filter, we get another phase-contingent association:

$$Q_{mj}[n]=A_{mj}\sin(2\pi f_m n/f_s+\Phi_{mj})\cdot A_r\cos(2\pi f_r n/f_s+\Phi_{ref})$$
$$Y_{mj}[n]=A_{mj}A_r(1/2)\{\sin(\phi_{mj}-\phi_{ref})\}=A_{mj}A_r(1/2)\{\sin(\theta_j)\} \quad (8)$$

If we now calculate the magnitude of the X and Y expressions, we obtain:

$$r_{mj}^2 = X_{mj}^2 + Y_{mj}^2 \quad (9)$$

$$r_{mj}^2 = SQRT(X_{mj}^2 + Y_{mj}^2)$$
$$= SQRT\{[(1/2)A_{mj}A_r]^2 \cdot [\cos^2(\theta_j)+\sin^2(\theta_j)]\}$$
$$= (1/2)A_{mj}A_r$$

This method yields a value that is independent of the phase differences and is directly related to the amplitude of channel j.

It is to be noted that, in some embodiments, the lock in detection can be, but is not limited to, a phase-insensitive quadrature method. Digital detection or lock-in techniques employing phase-diversity or phase-dependent detection, with or without utilizing a phase shifter, are also provided in some embodiments of the disclosed subject matter.

Extension of the above technique becomes a little more involved when one incorporates multiple wavelength imaging. Suppose, for example, that have two light sources modulated at f1=3 kHz and f2=5 kHz superimposed on one another. The resulting signal is the sum of the two individual sinusoids:

$$V_{f1}+V_{f2}=V_1\sin(f_1 t)+V_2\sin(f_2 t) \quad (10)$$

If one multiplies this signal with a single reference signal, say at frequency f1 (3 kHz), the product will consist of multiple components spread out across the frequency spectrum.
I) f1−f1=0 Hz=DC component
II) f1+f1=3 kHz+3 kHz=6 kHz
III) f2−f1=5 kHz−3 kHz=2 kHz
IV) f2+f1=5 kHz+3 kHz=8 kHz The only quantity we wish to preserve is the one straddling zero frequency. As has been shown before, this value is directly proportional to the amplitude of the optical input signal. The other frequency components should be eliminated via the low-pass filter. Elimination of the other frequency components can be achieved via a low-pass filter. Effective extraction of a single frequency band while suppressing all others, has direct implications on the bandwidth of the filter chosen and of the spacing between two modulation frequencies to ensure that none of the unwanted fractions falls into the passband of the filter.

In some embodiments, the lock-in filter can be an ordinary averaging filter. The following description, which references FIGS. 8-10, relates generally to a digital lock-in amplification scheme that is optimal for lock-in detection and optical imaging, including continuous wave (CW) imaging, according to some embodiments of the disclosed subject matter. In some embodiments, the digital lock-in amplification scheme is for simultaneously measuring amplitude and phase of multiple modulated optical signals used in continuous wave optical imaging. A digital lock-in algorithm according to some embodiments of the disclosed subject matter is described, including being described under certain sampling and modulation conditions, and results are shown for sample data. The detection scheme, after careful choice of sampling and modulation frequencies, can be excellent or ideal for isolating signals modulated by different frequencies. Its filter also provides good non-DC rejection vs. time response characteristics.

Figure 8:
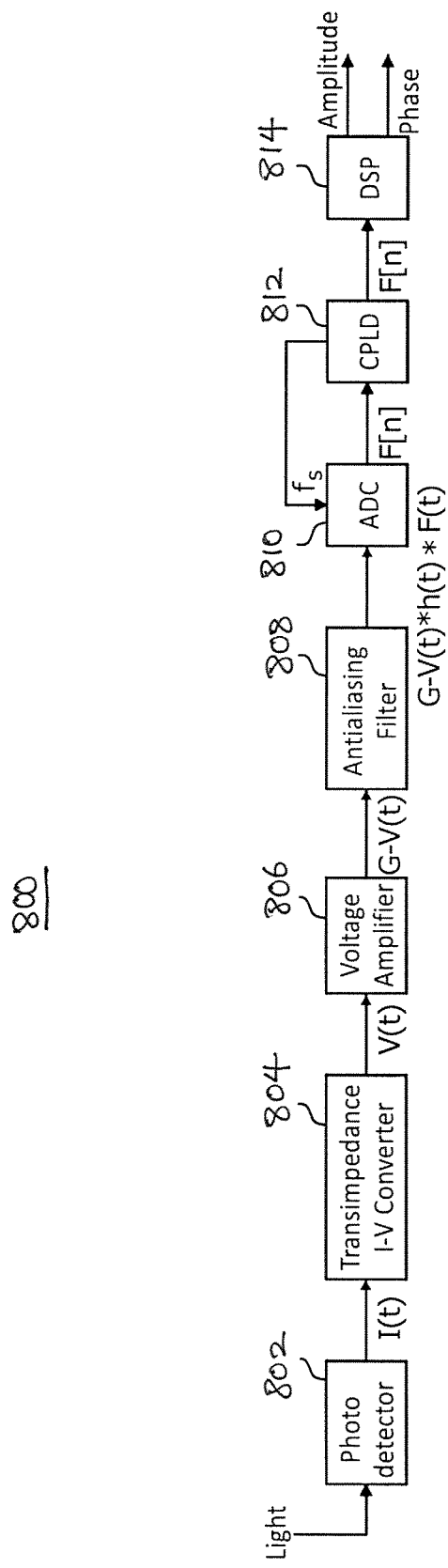
FIG. 8 is a block diagram depicting hardware components of a digital CW instrument, according to one embodiment of the disclosed subject matter.

FIG. 8 is a block diagram depicting hardware components 800 of a digital CW instrument, according to one embodiment of the disclosed subject matter. Photo detector 802 outputs a current signal, I(t), proportional to the incident light signal, which is then converted to a voltage, V(t), by a trans impedance I-V converter 804 and then amplified by a voltage amplifier 806 with gain G. An antialiasing filter 808, h(t), makes sure there are no frequencies above the Nyquist frequency. ADC 810 samples the signal, F(t), at a frequency $f_s$ controlled by a CPLD controller 812. The digital signal F[n] is then sent though the CPLD 812 on the way to DSP 814 where the lock-in algorithm, according to some embodiments of the disclosed subject matter, is performed and outputs the amplitude and phase for every modulation frequency.

According to some embodiments, every time an imaging system wants to measure the amplitude and phase of a signal, the lock-in algorithm actually takes $N_s$ samples at sampling frequency $f_s$. This means the data acquisition time is:

$$T_{acq}=N_s/f_s \quad (11)$$

Since the sampling is controlled by some digital controller with a clock frequency $f_{clk}$. Only certain values of fs are allowed:

$$f_s=f_{clk}/N_c \quad (12)$$

where $N_c$ is the integer number of clock cycles it takes the digital controller to run through a sampling period.

In some embodiments, in order for the averaging lock-in algorithm to work, the modulation frequency, fm, must be some integer multiple of:

$$T_{acq}^{-1}\cdot f_m=k\cdot f_s/N_s \quad (13)$$

With these constraints, one can use a simple $N_s$ point averaging filter:

$$g[n]=1/N_s \quad (14)$$

to both remove noise and isolate signals. The magnitude response of the averaging filter g[n] has a stopband attenuation of $20*\log(N_s)$ and can be approximated as:

$$|G(f)|=|\sin c(N_s\pi f/2f_s)| \quad (15)$$

which clearly has zeroes at $f=f_m$.

Instead of a reference signal, in some embodiments, the lock-in algorithm stores an Ns point sequence of $C_m[n]=\cos[2\pi f_m n/f_s]$ and $S_m[n]=\sin[2\pi f_m n/f_s]$, for every modulation frequency $f_m$. If the signal is:

$$F_m(t)=A_m\cos(2\pi f_m t+\phi_m) \quad (16)$$

then the digital signal is:

$$Fm[n]=A_m\cos[2\pi\pi_m n/fs+\phi_m]. \quad (17)$$

The first step of the algorithm is to modulate the signal by the stored sequences for every modulation frequency to produce 2 new sequences:

$$I_m[n]=C_m[n]\cdot F[n]=A_m/2\cdot\cos(\phi_m)+A_m/2\cdot\cos[4\pi f_m n/f_s+\phi m] \quad (18)$$

and:

$$Q_m[n]=S_m[n]\cdot F[n]=A_m/2\cdot\cos(\phi_m)+A_m/2\cdot\sin[4\pi f_m n/f_s+\phi_m]. \quad (19)$$

These sequences are then filtered by averaging filter. This is the same thing as taking the mean of the sequence to result in the following values:

$$X_m = \frac{1}{N}\sum_{n=1}^{N_s} I_m[n], \quad (20)$$

$$Y_m = \frac{1}{N}\sum_{n=1}^{N_s} Q_m[n]. \quad (21)$$

By equation (13) one can see that the mean is taken over k complete periods of F[n] and thus when the second non-dc terms in (18) and (19) are averaged over 2 k complete periods the result is zero. What are left are the quadrature components of the amplitude divided by 2 so that the amplitude is:

$$A_m = 2\sqrt{(X_m^2 + Y_m^2)}. \quad (22)$$

The phase $\phi_m$ is found by taking the Quadrant dependent inverse tan function $$\varphi_m = -\tan^{-1}\left(\frac{Y_m}{X_m}\right). \quad (23)$$

It is well known that the optimum filter for white noise suppression and DC retention is the averaging filter [4], but due to careful choice of sampling and modulation frequencies to the constraints in (13), according to some embodiments of the disclosed subject matter, it is also optimum for removing the any signals that are multiples of $f_s/N_s$. When using multiple modulated sources S(t) is actually:

$$F(t) = \sum_m A_m \cos(2\pi f_m t + \varphi_m). \quad (24)$$

Generally, with other lock-in filters the additional frequency components interfere with accurate measures of $A_m$ and $\phi_m$, but with the digital lock-in filter, according to some embodiments of the disclosed subject matter, these frequencies are zeroed out when averaged after being modulated by a reference sequence which is not of the same frequency. As a proof one can see the following is a consequence of (13) and (15).

$$G(f_i+f_j)=G(f_i-f_j)=0(i\approx j). \quad (25)$$

When signals are modulated together the resulting frequencies are the sum and difference of the two frequencies. If the original frequencies are not the same, the signals at the two new frequencies are zeroed by the averaging filter. This means that a source can be modulated by many frequencies without them interfering with each other.

Figure 9:
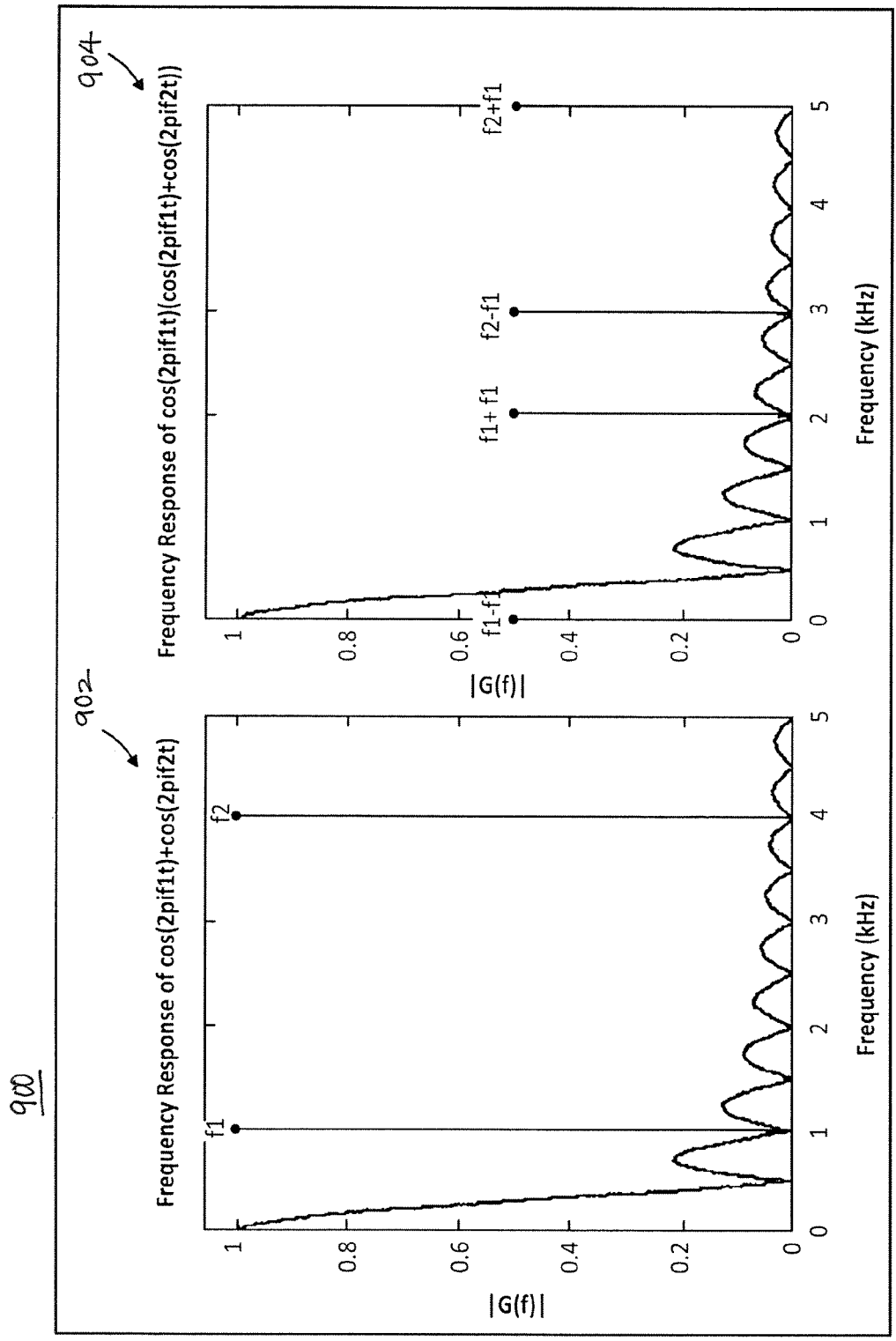
FIG. 9 is a set of graphs depicting frequency response of filter, original, and modulated signals, according to one embodiment of the disclosed subject matter.

FIG. 9 is a set 900 of graphs 902, 904 depicting frequency response of filter, original, and modulated signals, according to one embodiment of the disclosed subject matter. FIG. 9 shows that when a set of modulated signals are modulated by a reference, the only signal that does not fall into a zero bin is when the two signals have the same frequency. When frequencies other than specified are used, inaccurate measures of amplitude and phase result.

Figure 10:
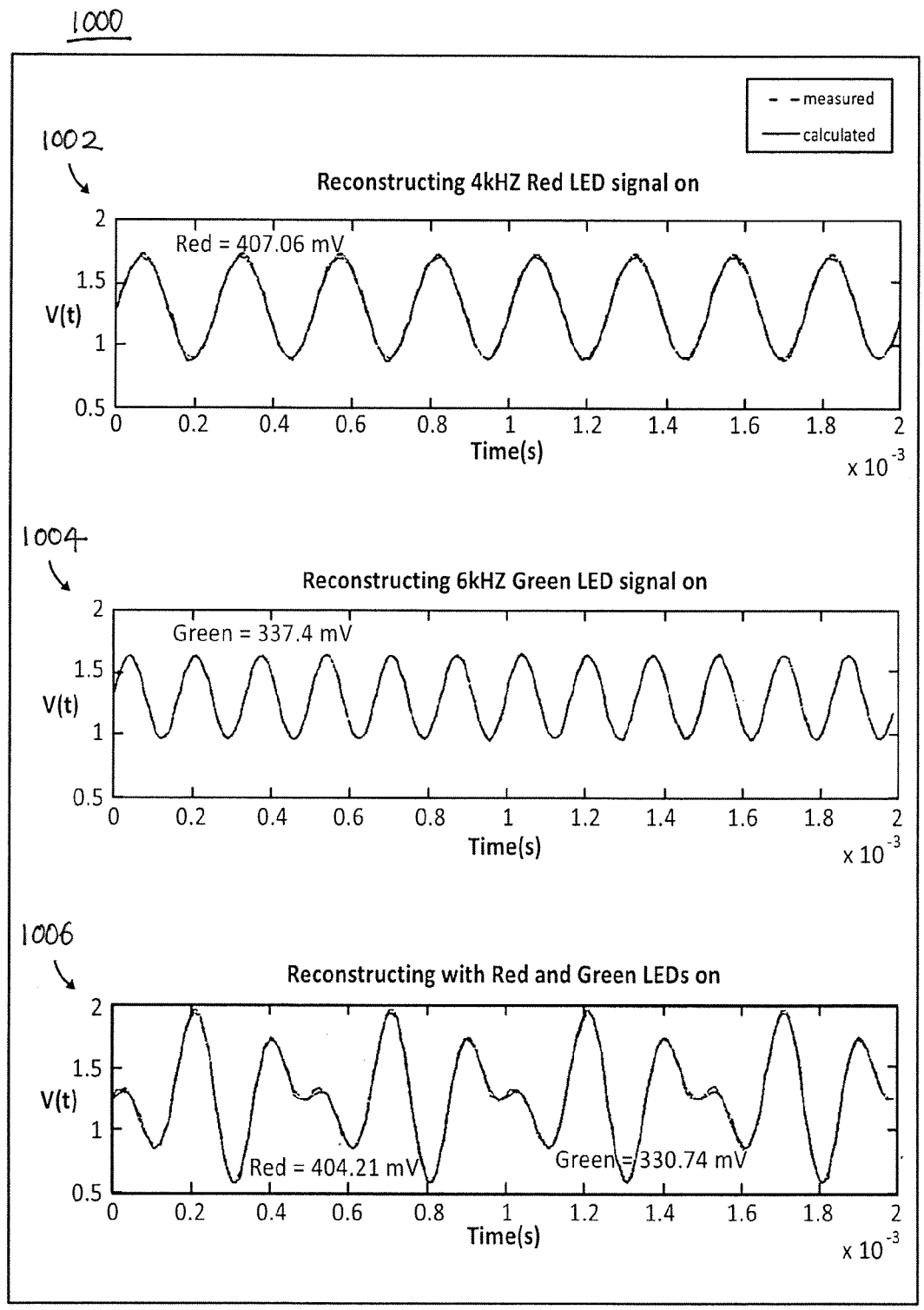
FIG. 10 is a set of graphs that depict plots of calculated signals along with the measured signals, according to one embodiment of the disclosed subject matter.

The following, including the description with reference to FIG. 10, relates to results of testing of a lock-in algorithm, according to some embodiments of the disclosed subject matter, on measurements. Red and green LED's were modulated in a very noisy environment by 4 kHz and 6 kHz wave respectively and the shown onto a single photo detector, such as the photodetector 802 depicted in FIG. 8. For convenience analog signals where sampled with an oscilloscope after the filter stage in FIG. 8. Data was saved to a disk and the algorithm was performed using MATLAB. The amplitudes of the signals were kept at a constant value or turned off completely. Measurements were taken with just the red LED on, just the green LED on, and both of them on. The calculated amplitude and phase were used to reconstruct the measured signals in order to verify that the results were correct.

FIG. 10 depicts a set 1000 of graphs 1002, 1004, 1006 that depict plots of these calculated signals, as described above, along with the measured signals. The graphs 1002, 1004, 1006 depict measured signals, calculated amplitudes, and reconstructed signals. Calculated amplitudes are shown by each plot.

It is to be noted that, with reference to FIGS. 8-10, while techniques are described primarily with reference to CW imaging, they can also be extended into the frequency domain.

The following provides description relating to circuit construction and signal conditioning to accommodate desired bandwidth, sensitivity, and temporal response, with regard to digital signal processing techniques used in optical tomography.

Numerous methods are currently used to collect and analyze light transmission data in optical tomographic imaging studies. The processes are categorized as time domain, frequency domain, and steady-state or CW domain. These techniques differ in the temporal characteristics of the illuminating source and hence their respective detection techniques. Each approach features unique benefits and deficiencies. Examples of instruments utilizing the various methods as well as advantages and disadvantages of the different approaches have been described in literature. Although the steady-state approach provides data with the least information content, it provides many benefits related to cost/performance issues.

Most existing instruments used to perform optical measurements utilize an analog scheme to collect, condition, and filter the incident signal. In some systems, analog phase-sensitive lock-in methods are employed to extricate the optical signal obscured by noise of potentially greater magnitude. Such analog detection systems, however, suffer from a number of deficiencies and limitations. More specifically, analog phase sensitive detection has many problems associated with it that adversely affect their performance and restrict subsequent applications. Some primary deficiencies include signal drift, output offsets, gain error, limited dynamic reserve, and harmonic rejection. Additionally, external parameters such as temperature or age contribute to analog noise and, consequently, measurement uncertainty. Furthermore, analog processing is notably sensitive to component tolerances thereby limiting functional utility. Finally, when the digital timing signals share a backplane with analog data signals, coupling can occur causing fluctuations along the analog lines. Consequently, the instrument noise floor is elevated, sensitivity is reduced, and dynamic range is diminished.

Figure 11:
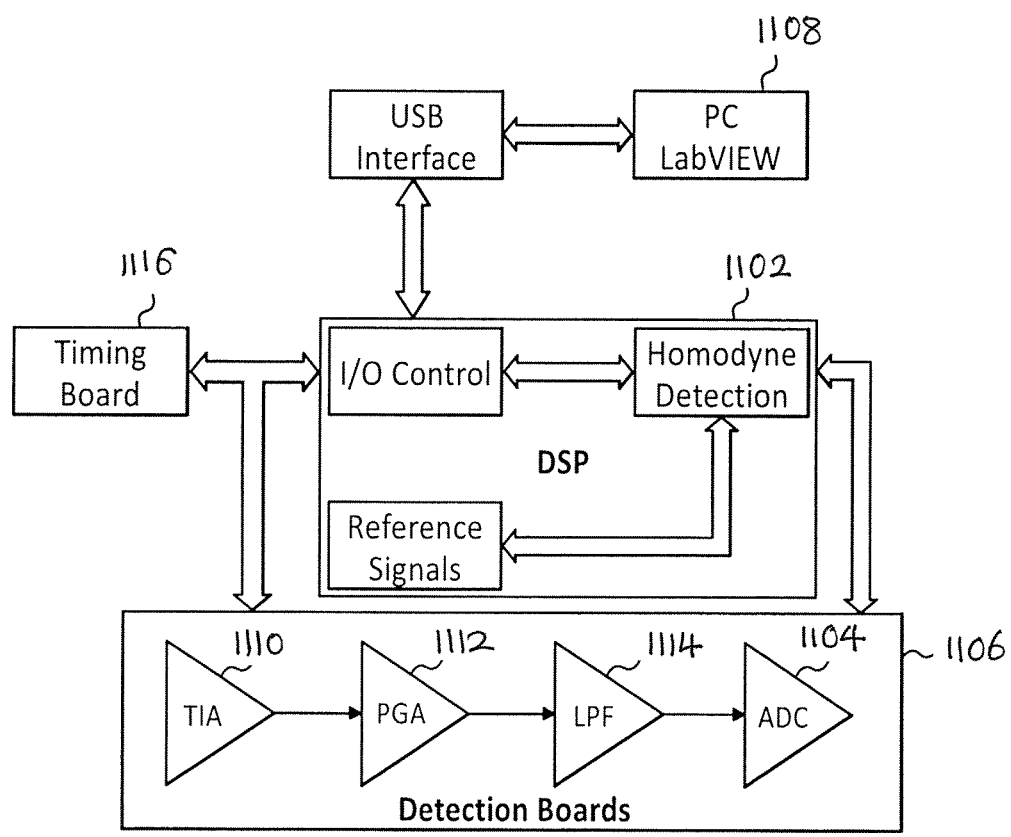
FIG. 11 is a block diagram depicting system layout and signal communication, according to one embodiment of the disclosed subject matter.

FIG. 11 is a block diagram 1100 depicting system layout and signal communication, according to one embodiment of the disclosed subject matter. DSP 1102 is the component by which the signals are collected, processed and filtered, and finally routed to a host PC 1108. In some embodiments, the system uses Model ADSP-21161 with Super Harvard Architecture Computer (SHARC), available from Analog Devices, Inc., whose key features include 600 MFLOPS peak, 32-bit and 40-bit floating point arithmetic and user-configurable 1 MBits on-chip SRAM memory. The system employs parallel detection to assist in achieving a high temporal resolution.

This particular embodiment accepts up to 32 independent detectors simultaneously whose distribution comprises 8 Printed Circuit Boards (PCB), each accommodating 4 channels, but as discussed below, systems can be implemented with more channels by using a system architecture that employs multiple DSP's. A single 4-channel high-speed 16-bit Analog to-Digital Converter (ADC) 1104 is mounted on each board 1106. A timing board 1116 consisting of the Complex Programmable Logic Device (CPLD), clock, and some support circuitry is interfaced with the DSP 1102 and detector boards 1106. The USB protocol is used to transfer data between the DSP 1102 and the host PC 1108. The USB chip with its support circuitry and interface glue logic is mounted on a separate PCB.

In some embodiments, the photodiode and trans-impedance amplifier 1110 of the system of FIG. 11 can be similar to those of the system described in Schmitz 2002. Silicone-based photodiodes provide the sensitivity, frequency response, and linearity requisite for the application. These attributes combined with their low cost and low dark current make them a good choice for the design.

The trans-impedance amplifier (TIA) 1110 was selected to keep the existing and inherent noise minimal. The feedback network of the TIA 1110 and a subsequent PGA 1112 stage offer a multitude of signal gain stages to provide a large global dynamic range for each channel and to maximize the resolution of the 16-bit ADC. A gain of 1, 10, or 10,000 kV/A is available from the TIA 1110 feedback while an additional gain of 1, 10, or 100 V/V is offered by the PGA yielding a dynamic range exceeding 120 dB and an absolute maximum signal gain of $10^9$ V/A (180 dB). A 16-bit ADC offers up to 0.0015% resolution full-scale, so the system can theoretically detect 0.76% fluctuations for signals as small as 10 pA, the approximate noise floor.

In some embodiments, before the analog signal is digitized, it is sent through a low-pass anti-aliasing filter 1114, so that the frequency spectrum conforms to the Nyquist limitation. Since the sampling rate is ~75 k samples/sec and the modulation frequencies of the lasers are from 1-9 kHz, the filter's impulse response can be enhanced at the expense of the frequency roll-off. The filter can be an 8th order Butterworth, which affords a balance between the time versus frequency response tradeoff. With a cutoff frequency of 12.5 kHz, one achieves 0.1% attenuation at the upper limit of modulation (9 kHz). By sampling at 75 ksps, noise above 67 kHz can alias into the passband. However, the filter attenuation at this frequency is ~117 dB which is adequate noise suppression. An impulse at the input of the LPF yields a filter settling time of 450 μsec, not a limiting factor in the general detection temporal response. Once the signal is filtered, it is digitized by a 16-bit SAR (Succession Approximation Register) Analog-to-Digital Converter 1104. The ADC has a 4-channel multiplexed input and a serial output which directly interfaces with the DSP 1102. Its maximum sampling rate of 1 Msps assures that every channel is sampled at the desired 75 ksps.

The detection scheme is based on an amplitude-modulated light source, which allows execution of the lock-in operation. As stated above, the digitized data signals from the detectors can be time-division-multiplexed onto a double serial line. Once the DSP 1102 receives the data from the ADC 1104, it collates the signals and performs the homodyne detection algorithm. This technique mixes the optical signal with a DSP-generated reference signal at an identical frequency and sends the output through a low-pass filter. The result is a DC signal whose magnitude is proportional to magnitudes of the optical power and reference voltage, and their phase difference. By mixing the original signal with both the in-phase and quadrature components of the reference, the final output is independent of phase difference and is only contingent on the amplitude of the inputs. In some embodiments, this is an attractive option for some systems as described herein, for example, since all channels do not share a common phase, which is an effect of the sampling sequence. The homodyne algorithm can be easily extended to accommodate multiple wavelengths, and the low-pass-filter 1114 is specifically designed with this consideration.

In the embodiment depicted in FIG. 11, a low-pass filter 1114 used for the lock-in stage is an ordinary averaging filter; however, in other embodiments, other filters may be used. By carefully choosing the sampling frequency, modulation frequencies and the number of samples acquired, the unique frequency response of this filter type can be exploited. Analysis and investigation of the filter's magnitude response, which is $|H(jw)|=\sin c(N_s w/2f_2)$, where $j=\sqrt{-1}$ and w is the angular frequency, reveals particular frequencies throughout the spectrum that are zeroed out. The relationship between these eliminated frequencies, sampling frequency, modulation frequencies, and number of samples is as follows.

$$f_{zero}=k[f_{Nyquist}/(N_s/2)]=k[f_s/(N_s)], f_m=f_{zero} \quad (26)$$

Where N is the number of samples acquired, k is any positive integer, $f_{Nyquist}=f_s/2$, and $f_m$ is the modulation frequency. $f_s$ and $N_s$ are chosen based on based on various resulting tradeoffs.

It is instructive to note practical and constructive consequences arising by adhering to the above correlations. Firstly, k complete periods are accumulated at that particular modulation frequency. This fact can be demonstrated by the following relationships:

$$T_m=T_{zero}=[(N_s/k)T_s], T_{acq}=N_s T_s, \text{ so } T_m=T_{acq}/k \text{ or } T_{acq}/T_m=k \quad (27)$$

Where $T_{acq}$ is he data acquisition period for a single channel, and $T_x$ is the period of parameter x. Secondly and significantly, the product of the detected light signal (with multiple modulation frequencies/wavelengths) and a single reference signal results in the cancellation of all additive frequency components except the one being "locked onto," which sits at DC.

Figure 12:
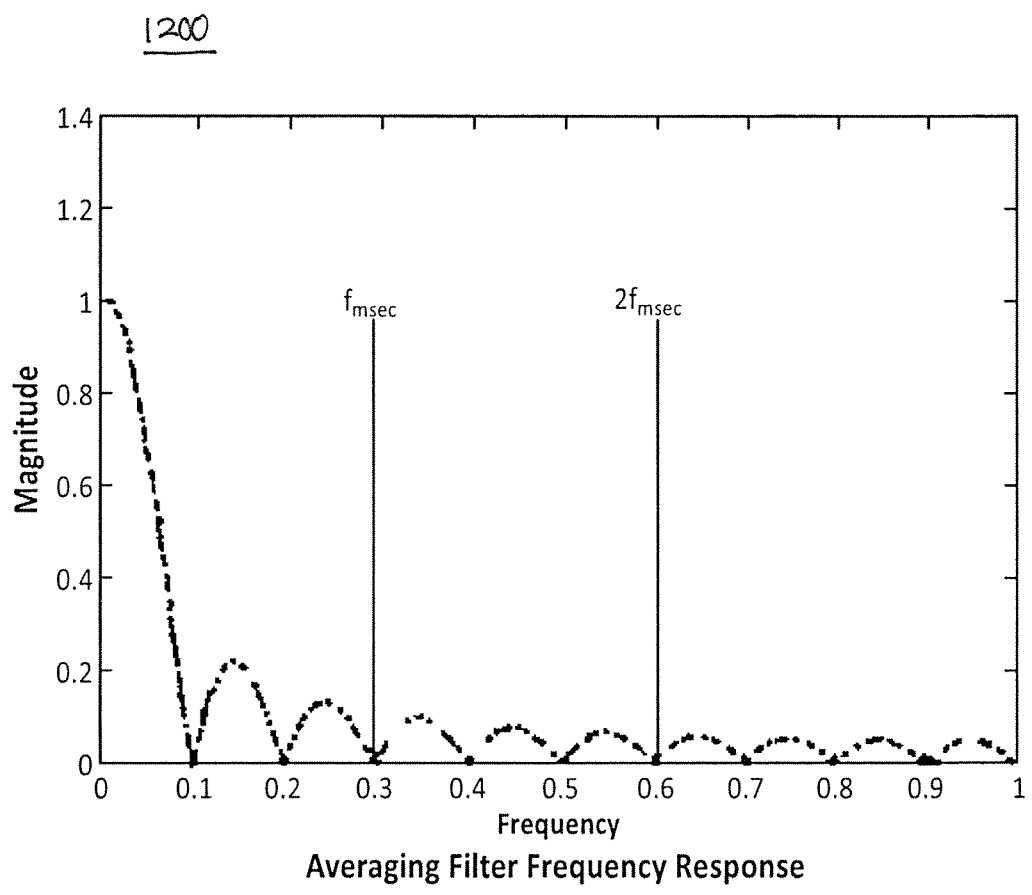
FIG. 12 is a graph 1200 depicting frequency response of a 20 point averaging filter, with the horizontal frequency axis running from zero to Nyquist frequency.

FIG. 12 is a graph 1200 depicting frequency response of a 20 point averaging filter, with the horizontal frequency axis running from zero to Nyquist frequency.

With respect to collecting data, once the DSP has completed its calculation, the data must be streamlined into the host computer. In some embodiments, because the DSP has many responsibilities and processes accessing its data busses and internal memory, immediately after performing the lock-in computations the DSP deposits the data values in an external memory bank. There, it can be accessed by a timed transfer protocol and directed to the host PC without causing a bottleneck in the digital processor. Furthermore, data latches and control circuitry are used to coordinate the gain-bits being downloaded from the host PC into the signal processor. To buffer the data transfers, bi-directional driver and transceiver devices can be implemented to all data transmissions. Streamlining measurement results or gain-bit values can be accomplished via a microcontroller-based USB digital data transfer. USB offer many distinct benefits, making it the interface-bus of choice. It makes the instrument portable, eliminates the need for a data-acquisition board, presents a plug-and-play design, and can support transfer speeds up to 480 Mb/s. Providing this simple user experience for data connectivity requires some inner complexity and adds a protocol layer to the system interface. LabVIEW is the PC control software, available from National Instruments Corp., which integrates embedded C-code to communicate with the USB's microcontroller. The timing sequences required for data transfers between the host PC and DSP are synchronized by a designated controller or programmable logic device. The DSP can take the form of an embedded DSP, which means that it is not integrated into the host computer.

One of the challenges to the system design is orchestrating the multitude of events transpiring for each imaging frame. For every source position, the gain bits must be updated for each detector channel, and the settling time of the optical switch and the analog electronics must be considered. The sampling of the detectors must be synchronized, so they can be efficiently streamlined into the DSP 1102 in a time-division multiplexed fashion. The objective is to multiplex 32 channels, 200 samples/channel, and 16 bits/sample into a single serial port in 2 msec. These functions are executed by a high-performance Complex Programmable Logic Device (CPLD). This device acts as a multi-level state machine, and can simulate a variety of standard logic operations. Among other functions, during the imaging routine the CPLD is responsible for triggering the sampling process of the ADC's and for sequentially accessing the digitized data so that it can be time-division multiplexed into the DSP.

Figure 13:
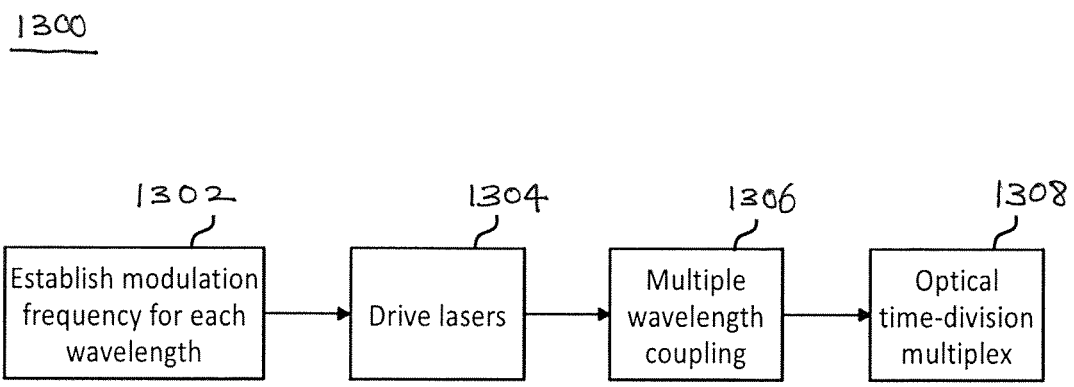
FIG. 13 is a flow diagram depicting a method 1300 according to one embodiment of the disclosed subject matter.

FIG. 13 is a flow diagram depicting a method 1300 according to one embodiment of the disclosed subject matter, for generating multi-wavelength illuminating sources at multiple locales, as required for attaining spectroscopic tomography.

Step 1302 includes establishing modulation frequency for each wavelength.

Step 1304 includes driving lasers.

Step 1304 includes performing multiple wavelength coupling.

Step 1306 includes optical time-division multiplexing.

In some embodiments, since a phase sensitive detection scheme is employed to extract the amplitude of the optical signal, it is required to amplitude-modulate the light source that probes the tissue and provide a reference frequency equal to and phase-locked with the modulation frequency. When using multiple wavelengths simultaneously, each requires their own distinct modulation frequency to encode the optical intensity and reference signals to decode it.

In some embodiments, to generate a modulation frequency, direct digital synthesis (DDS) technology is used. Direct digital synthesis is a method of producing an analog sine waveform by generating a time-varying signal in digital form and then performing a digital-to-analog conversion. Because operations within a DDS device are primarily digital, it can offer fast switching between output frequencies, fine frequency resolution, and operation over a broad spectrum of frequencies. With advances in design and process technology, modern day DDS devices are very compact and consume little power. It therefore serves as a stable and accurate waveform generator to produce the frequency stimulus required for the application. Each DDS device outputs one frequency and therefore supplies only a single illuminating wavelength.

In some embodiments, the design uses a synthesizer that provides two sine waves, in-phase and quadrature, which are 90 degrees phase shifted from each other. This provides the option of sampling both components to use as the reference signals in quadrature lock-in detection, as described in detail above. In some embodiments, the first choice is to digitally generate these reference signals internally in the DSP thereby utilizing the DDS synthesizers only to modulate the lasers. In some embodiments, however, other options may be utilized, such as digitizing the analog reference waveforms instead.

In some embodiments, the DDS contains dual integrated 12-bit digital-to-analog (DAC) converters for high resolution waveforms and demonstrates excellent dynamic performance. A low pass filter is applied to the produced waveform in an effort to lower the harmonic content even further and make efficient use of the higher precision 16-bit analog-to-digital converters (ADC) used for sampling the detector channels.

In some embodiments, the function of the digital synthesizer is determined and controlled through a set of register values together with specified commands. A designated microcontroller is assigned to interfacing directly with the DDS chips. Programming the relevant instructions required for generating specific waveforms as well as timing organization will be executed via this controller and/or the digital signal processor. Selecting the modulation frequencies can be preprogrammed into the controller or modified spontaneously through computer software or autonomous devices, for example.

Some embodiments provide an instrument that uses laser diodes in the near-infrared region as the radiative source for optical imaging. The lasers are regulated by select OEM laser diode controllers that combine a low noise, low drift current source with a precise thermoelectric cooler (TEC). Operating in constant current mode creates a laser output whose power is proportional to the driving current. Therefore, once the respective frequencies are generated, one can use them to modulate the driving current of the light source, which in effect, modulates the laser output.

In an effort to quantify hemoglobin parameters and other biological chromophores, light transmission data must be collected on multiple wavelengths. The minimum number of wavelengths for performing spectral analysis is two. By combining these wavelengths together and making simultaneous measurements, one can shorten the data acquisition period and increase the temporal response of the instrument. To accomplish this, according to some embodiments, one can use either an independent optical coupler which effectively merges the light from multiple wavelengths or by means of discrete geometric optics components such as beam splitters and/or dichroic mirrors.

In some embodiments, once the light source is modulated, controlled, driven, and combined, the system performs spatial encoding of multiple illumination locales around the target being probed. A method frequently employed to separate source locations is through time-division multiplexing of the combined light source. This can be realized by a 1×N optical switch where N is the number of different source positions. A single input is routed to a distinct output which is controlled by a specific address. When the switch receives an appropriate address, the input is aligned with the respective output. The settling time of the switch is on the order of 2-5 msec, which is advantageous for acquiring dynamic images.

A problem with commercially available switches is that the inter-channel crosstalk is only specified to about −50 to −60 dB while the dynamic range of the instrument is effectively around 90 dB of optical power (when comparably adjusted). This means that light can leak from one channel to another contaminating the measured quantity.

Figure 14:
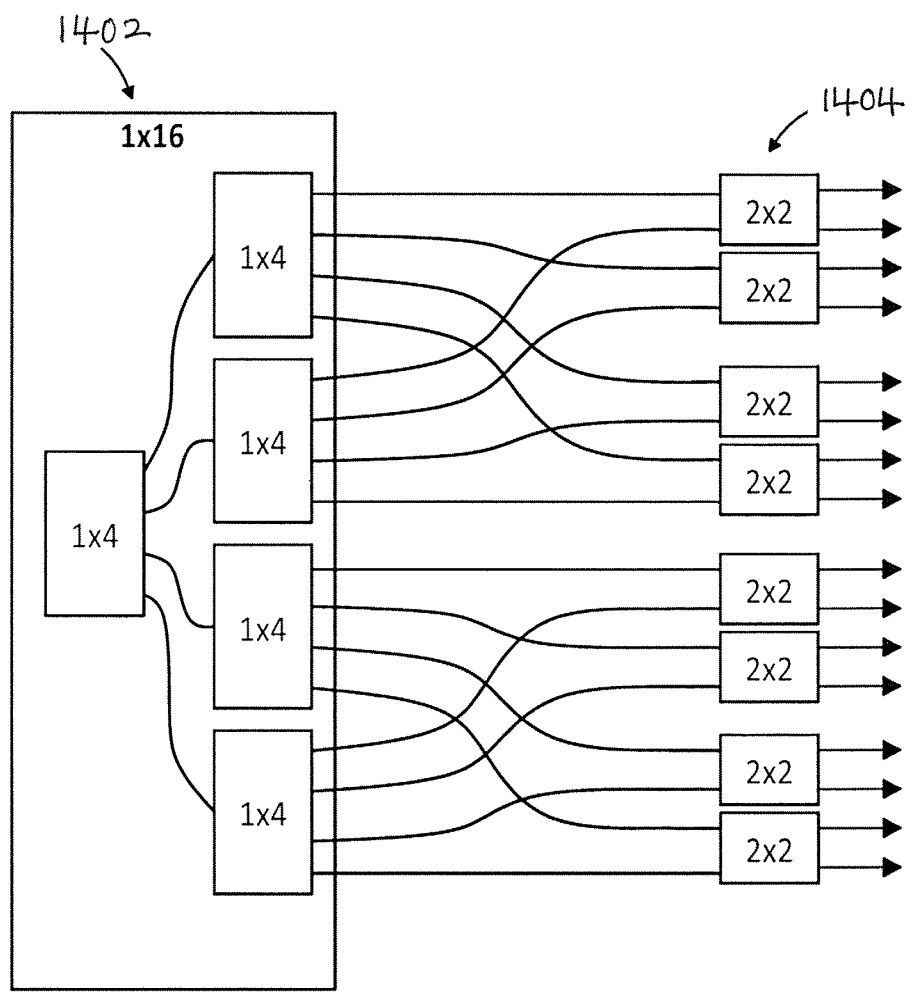
FIG. 14 is a block diagram depicting an optical switch, according to one embodiment of the disclosed subject matter.

FIG. 14 depicts one embodiment of a configuration to address this problem. Specifically, FIG. 14 is a block diagram 1400 depicting a 1×16 optical switch 1402 in series with 8-2×2 switches 1404 to provide a composite 1×16 multiplexed source architecture with an effective crosstalk elimination of over 100 dB. As such, in some embodiments, a fast optical 1×N optical switch (N=number of output source positions) with switching time on the order of 2-5 msec can be utilized to achieve over 100 dB of crosstalk isolation by judiciously cascading multiple switching stages.

In some embodiments, the output of the optical switch then interfaces directly with the tissue or measurement probe. This entire apparatus can function independently or be controlled by a personal computer, for example. Offering variable parameter control will allow for spontaneous user command. Also, an LCD display may be integrated into this setup to provide the user with some system monitoring and feedback.

There is a need for a digital optical tomographic imaging system having an increased number of sources and detectors while still maintaining high data throughput and fast imaging rates. For example, large numbers of source/detector pairs are necessary for imaging both breasts or both hemispheres of the brain simultaneously. Also, fast imaging rates enable the observation of the transient response of the tissue in response to external stimulus, such as a Valsalva maneuver, application of pressure, and pure oxygen breathing as well as visual stimulation for brain imaging.

As described below, an increased number of detectors with high imaging speed can be accomplished with a master/slave digital signal processors (DSP) architecture that can coordinate the throughput of the data processing, in which a master DSP is configured to coordinate the input and detection systems. A hybrid serial/parallel interface can be also employed to facilitate high speed data throughput. In addition, a master/slave complex programmable logic device (CPLD) architecture can coordinate the sequencing of the signals for the detection timing and sequencing.

As the number of detectors, and thus the amount of the detected data, is increased, the processing capacity also has to be increased to maintain the imaging rate. The processing capacity may be increased, for example, by adding more digital signal processors. However, this also increases the communication and control overhead due to the increased system complexity. A digital optical tomographic imaging system implementing the master/slave DSP architecture allows more flexible scalability without having to sacrifice the fast imaging rate.

Figure 15:
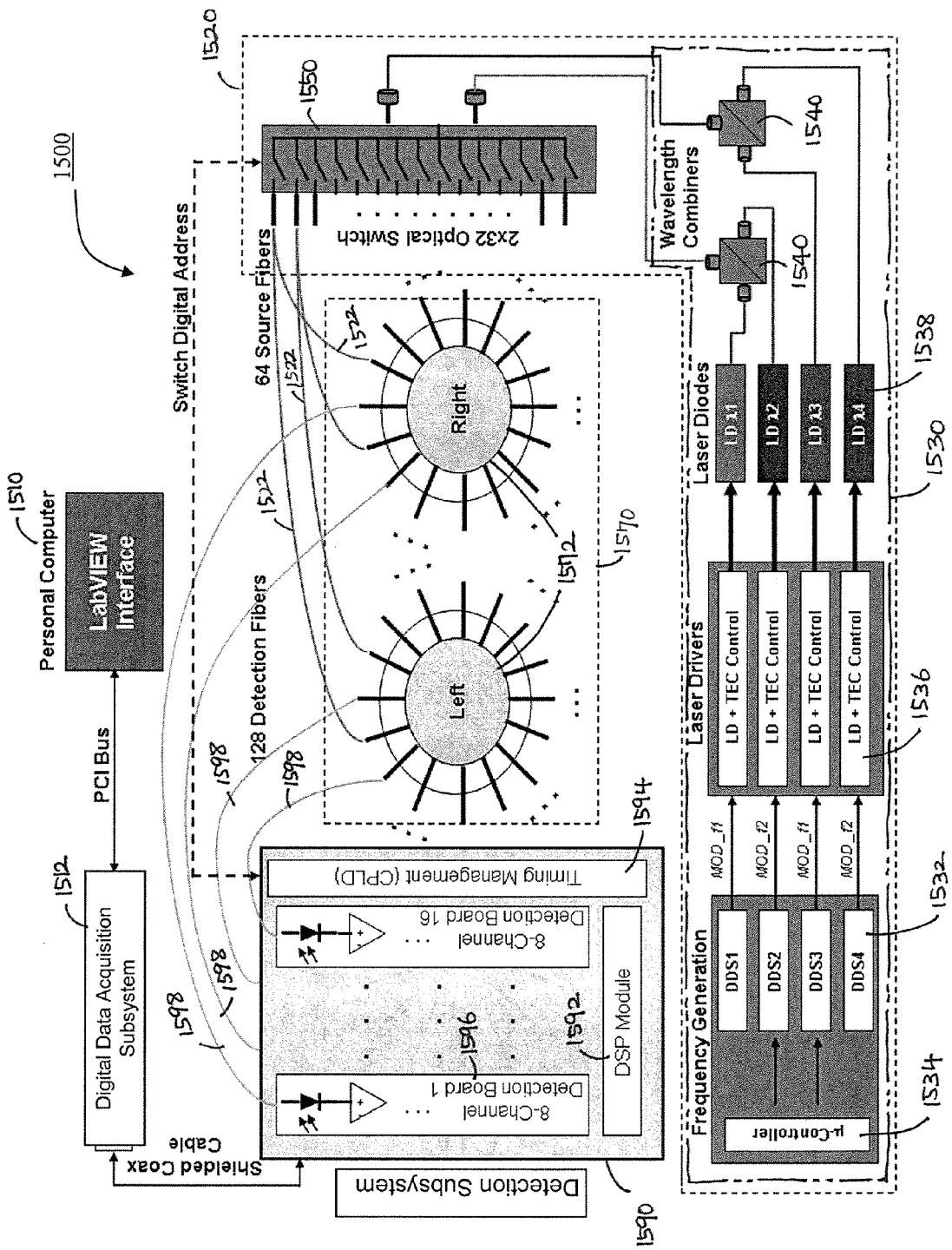
FIG. 15 illustrates a digital optical tomographic system in accordance with one embodiment of the disclosed subject matter.

Referring to FIG. 15, an embodiment of digital optical tomographic imaging system 1500 can include a host computer 1510, a light delivery subsystem 1520, and light detection subsystem 1590. The light delivery subsystem 1520 in turn can include a plurality of source fibers 1522, a light generation subsystem 1530, a switch subsystem 1550, and a measurement subsystem 1570. The light detection subsystem 1590 can implement the master/slave DSP architecture, as described in further detail below.

The host computer 1510 can include a data acquisition subsystem 1512 and various input and output devices (not shown), such as display monitor, keyboards, and mouse for user interface. The host computer 1510 communicates with the rest of the system 1500 via data acquisition subsystem 1512. In some embodiments, the data acquisition subsystem can be a data acquisition circuit board manufactured by National Instrument® (NI) installed in a host computer running NI's LabView® software application. Alternatively, in some embodiments, an externally connected data acquisition subsystem can be used.

In some embodiments, a parallel data acquisition architecture is employed for communication between the host computer 1510 and the light detection subsystem 1590 to achieve high temporal resolution for real-time, dynamic and multi-channel imaging. For instance, the data acquisition subsystem 1512 can streamline demodulated signal from the detection subsystem 1590 through 32-bit parallel data lines that are grouped into separate ports as either input or output, while handshaking protocols are employed to govern data transfer with 20 MHz maximum internal sampling rate.

In some embodiments, more than one data acquisition subsystem is used to relay the data from the light detection subsystem 1590 to the host computer 1510 to accommodate an increased number of detectors, sources, and/or wavelengths.

The host computer 1510 is responsible for the user interface that allows the user to control the system 1500 as well as to monitor the measured data. For instance, users are able to control the laser output and detection performance through a Lab View® interface running on the host computer 1510. In some embodiments, the host computer 1510 is a dedicated computer that manages the operational control and data reconstruction.

The light generation subsystem 1530 can include one or more direct digital synthesis (DDS) chips 1532, one or more laser diodes 1538 that are controlled in part by corresponding laser drivers 1536, one or more optical combiners 1540, and a microcontroller chip 1534. The role of the light generation subsystem 1530 is to generate the light stream that is sequentially passed to the source fibers 1522 through the switching subsystem 1550. The switching subsystem 1550 is responsible for switching each input light stream between the source fibers 1522 that are brought into contact with the tissue using the measurement subsystem 1570.

In some embodiments, the system 1500 uses four wavelengths of light that are generated using the laser diodes 1538. For instance, four frequency encoded wavelengths of light may be 765 nm, 808 nm, 827 nm, and 905 nm. In some embodiments, an optical signal can be time and frequency multiplexed. For example, an optical signal of wavelength 765 nm can be amplitude-modulated at a first frequency and an optical signal of wavelength 808 nm can be amplitude-modulated at a second frequency. Then the 765 nm light and the 808 nm light can be combined into one light illumination stream (light stream A). And an optical signal of wavelength 827 nm can be amplitude-modulated at the first frequency and an optical signal of wavelength 905 nm can be amplitude-modulated at the second frequency. Then the 827 nm and the 905 nm light stream can be combined into another light illumination stream (light stream B). Then the tissue can be sequentially illuminated by light stream A followed by light stream B.

By imaging at multiple wavelengths of light in the visible to NIR range, it is possible to gain insight into the concentration of certain chromophores, such as oxy- and deoxy-hemoglobin, lipid, and water. As a result, changes in the chromophore levels in the proximity of breast tumors due to the increased vascularization and metabolic activity of the tumors can be observed.

The laser diodes 1538 are driven with amplitude modulated current input to produce an intensity-modulated output. The modulation frequency, in some embodiments, is in the kilohertz range. In one embodiment, for instance, the modulation frequency is in 5-7 kHz range. Each amplitude modulated current is generated using a DDS chip 1532 that can produce a very precise and stable output frequency. A specific frequency can be programmed to the DDS chip 1532 using the microcontroller chip 1534. The laser light from the laser diodes 1538 are then combined into one of multiple light streams using the optical combiners 1540, forming one beam for the switch subsystem 1550 to perform time-division multiplexing. The light stream is then fed into the switch subsystem 1550. In some embodiments, the switching subsystem 1550 comprises an optical switch.

The measurement subsystem 1570 can include one or more measuring heads 1572. The system 1500 can be used for a variety of applications depending on the configuration of the measurement subsystem 1570. For breast imaging, for instance, the measuring heads 1572 can be fluid filled cups where a patient lies facing down, and the breasts sit in the cups. The measuring heads 1572 also can be plates that compress the breasts in a manner similar to a mammogram imaging. In such a case, the source fibers 1522 can be attached to the plates, and the source fibers 1522 can make direct contact with each side of the compressed breasts. The measurement heads 1572 can also be a set of levers that bring the source fibers 1522 into contact with the breasts, where the source fibers 1522 surround the entire breasts and are in direct contact with the breasts. For brain imaging, the measuring heads 1572 can be a helmet or headband that can be used to bring the source fibers 1522 into contact with the scalp.

The light detection subsystem 1590 can include at least one digital signal processing (DSP) module 1592, a complex programmable logic device (CPLD) 1594, and a plurality of detectors 1596, each of which is connected to at least one detection fiber 1598. The light detection subsystem 1590 is responsible for detecting light signals and amplifying and filtering the detected signals. The detection fibers 1598 bring the detected light from the tissue to the silicon photodiodes located on the corresponding detectors 1596.

In some embodiments, there can be 16 detectors, although the number of detectors can vary significantly. Each detector 1596 has at least one detection channel. In some embodiments, a detector having 8 separate detection channels can be used. Each detection channel begins with a silicon photodiode to convert the incoming photons into a current, followed by a trans-impedance amplifier and a programmable gain amplifier to bring the signal up to an acceptable range for the analog-to-digital converter. In some embodiments, the detector 1596 can be a detection circuit board.

Immediately prior to the analog-to-digital converter, the signal is low-pass-filtered to remove any high frequency noise. This also serves as an anti-aliasing filter to prevent any aliasing during quantization. In some embodiments, a 4th-order Butterworth low-pass filter is used. In some embodiments, the signal is digitized using an Analog Devices AD 7655, which is a multiplexing analog-to-digital converter (ADC). It is capable of digitizing four channels in a sequential manner at very high rates. In some embodiments, the system 1500 takes 150 samples per channel with the ADC running at 75 kHz to give a total time to collect the samples of 2 ms.

Once the signal is digitized, the digital signal is passed to the DSP module 1592. The signal brought into the DSP module 1592 is demodulated into its component wavelengths prior to filtering and passing the measured amplitudes on to the host computer 1510. In some embodiments, the demodulation is performed using a digital lock-in detection technique.

The DSP module 1592 is responsible for passing the demodulated values to the host computer 1510 for reconstruction. In some embodiments, this is accomplished by using a first-in-first-out (FIFO) storage chip, which stores data until the host computer 1510 is ready to read from it. In some embodiments, the host computer 1510 continuously polls an Empty/Full flag on the FIFO to determine when it needs to read the data.

The DSP module 1592 is responsible for orchestrating all of the interactions between the host computer 1510 and the rest of the system 1500. The DSP module 1592 is also responsible for coordinating the input signal and the light detection subsystem 1590 to keep all measurements in synchrony. In some embodiments, the DSP module 1592 includes a high-performance 32-bit floating point DSP, ADSP-21161N, made by Analog Devices, Inc., featuring a Super Harvard Architecture (SHARC) core. With a single-instruction-multiple-data (SIMD) structure operating at 100 MHz, this device can carry out 600 million math operations per second. Its direct memory access (DMA) capability frees the processor core from intervening block data transfer between memories and interfaces, providing great flexibility when dealing with millions of bits of imaging data.

In some embodiments, the DSP module 1592 has more than one DSP. All of the DSPs may participate in the detection processing, but one of them, designated as the master DSP, may be responsible for the timing and sequencing control operations. For instance, a digital optical tomographic dynamic breast imaging system may have one master DSP and three slave DSPs. The master DSP works closely with the CPLD 1594 that assists the master DSP with the timing of many events that are part of the system 1500 operation.

In some embodiments, the DSP module 1592 includes more than one CPLD 1594, including one master CPLD and one or more slave CPLDs to assist the master DSP with the timing of the system 1500. In some embodiments, the master and slave DSPs and CPLDs can be split into two separate subsystems—one including master DSP and CPLD and the other including slave DSPs and CPLDs.

In summary, the light generation subsystem 1530 generates a light stream that is sequentially passed to the source fibers 1522 through the switching subsystem 1550. First the one or more DDSs 1532 generate very precise and stable output frequencies. The laser diodes 1538, which are driven by the laser drivers 1536 with amplitude-modulated current input, then produce intensity-modulated outputs. The outputs are then combined into one of multiple light streams using the optical combiners 1540. The switch subsystem 1550 then switches each input light stream between the source fibers 1522 using time-multiplexing technique.

Each detection channel of the detectors 1596 in the light detection subsystem 1590 begins with a silicon photodiode to convert the incoming photons into a current. The converted current is then amplified and low-pass-filtered by the detectors 1596 for analog-to-digital conversion. The detectors 1596 then digitize the amplified/filtered signal. Once the signal is digitized, the digital signal is sent to the DSP module 1592. The DSP module 1592 demodulates, filters, and further processes the digital signal before sending it to the host computer 1510 for display and storage. The DSP module 1592 also supplies timing and control signals to the rest of the system 1500.

Figure 16:
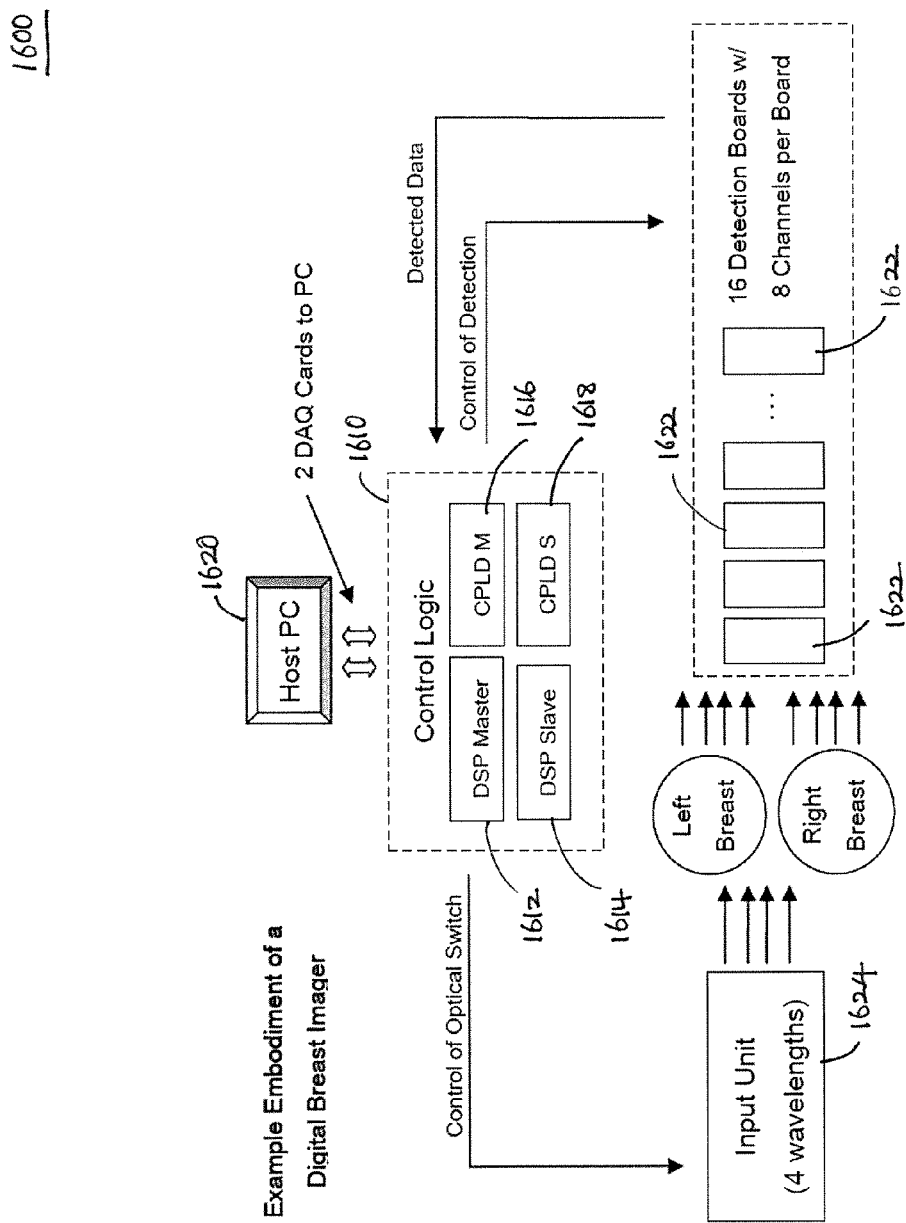
FIG. 16 illustrates a digital optical tomography system employing multiple digital signal processors in accordance with one embodiment of the disclosed subject matter.

Referring to FIG. 16, an embodiment of a digital optical tomographic dynamic breast imaging system 1600 is illustrated. The dynamic breast imaging system 1600 can include a host computer 1620 and an embedded digital signal processors-based module 1610 having a master digital signal processing subsystem 1612 and a slave digital processing subsystem 1614. The master digital signal processing subsystem 1612 can include a CPLD, referred to as master CPLD 1616. The slave digital signal processing subsystem 1614 can also include one or more CPLDs, referred to as slave CPLDs 1618.

The master/slave DSP architecture is designed in part to increase the data processing capacity of the system 1600. The increased data processing capacity in turn can lead to increased data traffic between the DSP module 1610 and the host computer 1620. This increased data traffic can be handled by adding additional data acquisition subsystems, such as data acquisition circuit boards. Alternatively, the master and slave DSP subsystems 1612, 1614 can be configured to share one data acquisition subsystem. In some embodiments, for instance, the system 1600 uses a hybrid serial/parallel interface. For instance, the DSP subsystems 1612, 1614 can share the parallel interface to the host computer 1620 even though there are not enough parallel bits to transmit the entire number of parallel bits of data at once. For example, the data can be segmented into smaller packets that are then sent serially along the parallel interface. The host computer 1620 then can reassemble the packets.

The master digital signal processing subsystem 1612 controls the slave digital signal processing subsystem 1614 by providing timing and control signals for the processing of input digital signals. The master DSP and CPLD 1612, 1616 can control programmable gain amplifiers in detectors 1622 to amplify the analog input signals. They can also supply timing signals to analog-to-digital converters in the detectors 1622. They can also control optical signal sources in input unit 1624.

Figure 17:
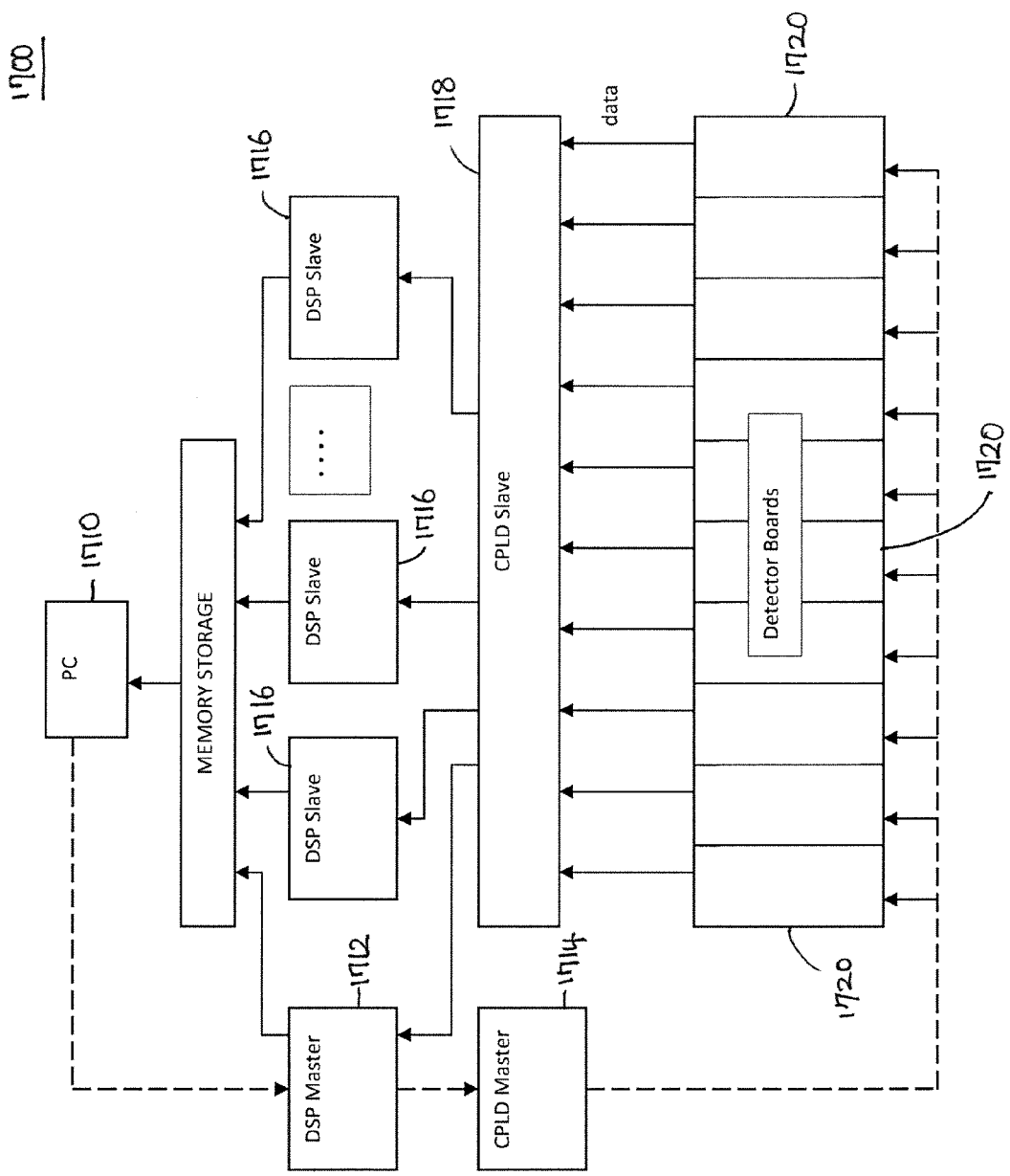
FIG. 17 is a diagram showing the flow of control signals and data in a digital optical tomography system employing multiple digital signal processors in accordance with one embodiment of the disclosed subject matter.

Referring to FIG. 17, a diagram showing the flow of control signals and data in a digital optical tomography system 1700 employing multiple digital signal processors is shown. When the system 1700 is powered up, the mater CPLD 1714 and one or more slave CPLDs 1718 are initialized. Interrupt vectors are set up for the master DSP 1712 and one or more slave DSPs 1716. The programmable digital input/output (I/O) lines for the master DSP 1712 and the slave DSPs 1716 are initialized. The serial port registers for the master DSP 1712 and the slave DSPs 1716 are cleared and then programmed. The imaging DMAs for the master DSP 1712 and the slave DSPs 1716 are set up. A timer for the master DSP 1712 is set up, followed by the setup of the external port buffers for the master DSP 1712 and the slave DSPs 1716. Reference signals for each wavelength are generated for the master DSP 1712 and the slave DSPs 1716. The master DSP 1712 and the slave DSPs 1716 enter the standby mode. In some embodiments, the master DSP 1712 in standby mode continuously polls the digital I/O lines connected to the host computer 1710, waiting for an instruction, such as 'acquire image' instruction, 'download gain bits' instruction, and 'download imaging parameters.

When the 'download imaging parameters' instruction issues, the master DSP 1712 receives imaging parameters, such as number of sources and detectors, gain bits, etc., from the host computer 1710 over the data bus through a relevant transfer protocol and stores them in the master DSP 1712 onboard memory. The imaging parameters are sent to the master CPLDs 1714 and are stored in the onboard memory of the master CPLD 1714 as well.

When the 'download gain bits' instruction issues, the master DSP 1712 receives the gain bit values from the host computer 1710 over the data bus and stores them in the master DSP 1712 onboard memory. The master DSP 1712 sends instruction words to the master CPLD 1714 and instructs it to go through the gain-upload sequence. The gain bits for all detection channels are sent out from the master DSP 1712 one source at a time and are routed to the detectors 1720 by the master CPLD 1714. The master DSP 1712 increments through the number of sources and stops when all gain bits are uploaded. In some embodiments, the gain bits are sent out over serial port transmit lines using the DMA protocol so that the master DSP 1712 core is not occupied with these I/O responsibilities.

When the 'acquire images' instruction issues, the master DSP 1712 sends an instruction word to both the master CPLD 1714 and the slave CPLDs 1718, indicating that the imaging process will begin. The master DSP 1712 initializes a timer for the electronics and light sources to settle. In some embodiments, the timer is set to 5 ms. The master DSP 1712 and the slave DSPs 1716 set up a serial-port to receive the digitized samples for the detector channels via DMA protocol. Each DSP 1712, 1716 is responsible receiving the digitized sample for a fraction of the detector channels. The master DSP 1712 awaits the timer interrupt and disables the timer in response. The master CPLD 1714 initiates and controls the sampling process. The detected data from multiple channels is fed through the slave CPLDs 1718, where it is multiplexed into a serial data stream for each DSP 1712, 1716. Each DSP 1712, 1716 has a DMA channel that is set up to collect the samples for each channel, so that when the sampling is complete, the data is organized in the DSP's 1712, 1716 memory block.

When all the data is received, each DSP 1712, 1716 independently runs its lock-in algorithm to demodulate the data by mixing reference signals with the data samples and filtering the resulting signal with an averaging filter, which discards the higher frequency components. Once the processing is complete, the mater DSP 1712 and the slave DSPs 1716 sends data to a memory storage 1722, such as a FIFO memory. Once the data is stored in the memory storage 1722, the host computer 1710 retrieves the data from the memory storage 1722. In some embodiments, there is a unique memory storage 1722 for each DSP 1712, 1716. In some embodiments, the memory storage 1722 is shared amongst the DSPs 1712, 1716.

These steps are repeated for all sources until the imaging frames is complete. After data from the last source is received, the master DSP 1712 checks the digital I/O status line to determine if it should image another frame. If control lines indicate the termination of data acquisition, then the master DSP 1712 completes the frame it is processing, instructs the master CPLD 1714, the slave CPLDs 1717, and the slave DSPs to stop, and return to the standby mode.

Figure 18:
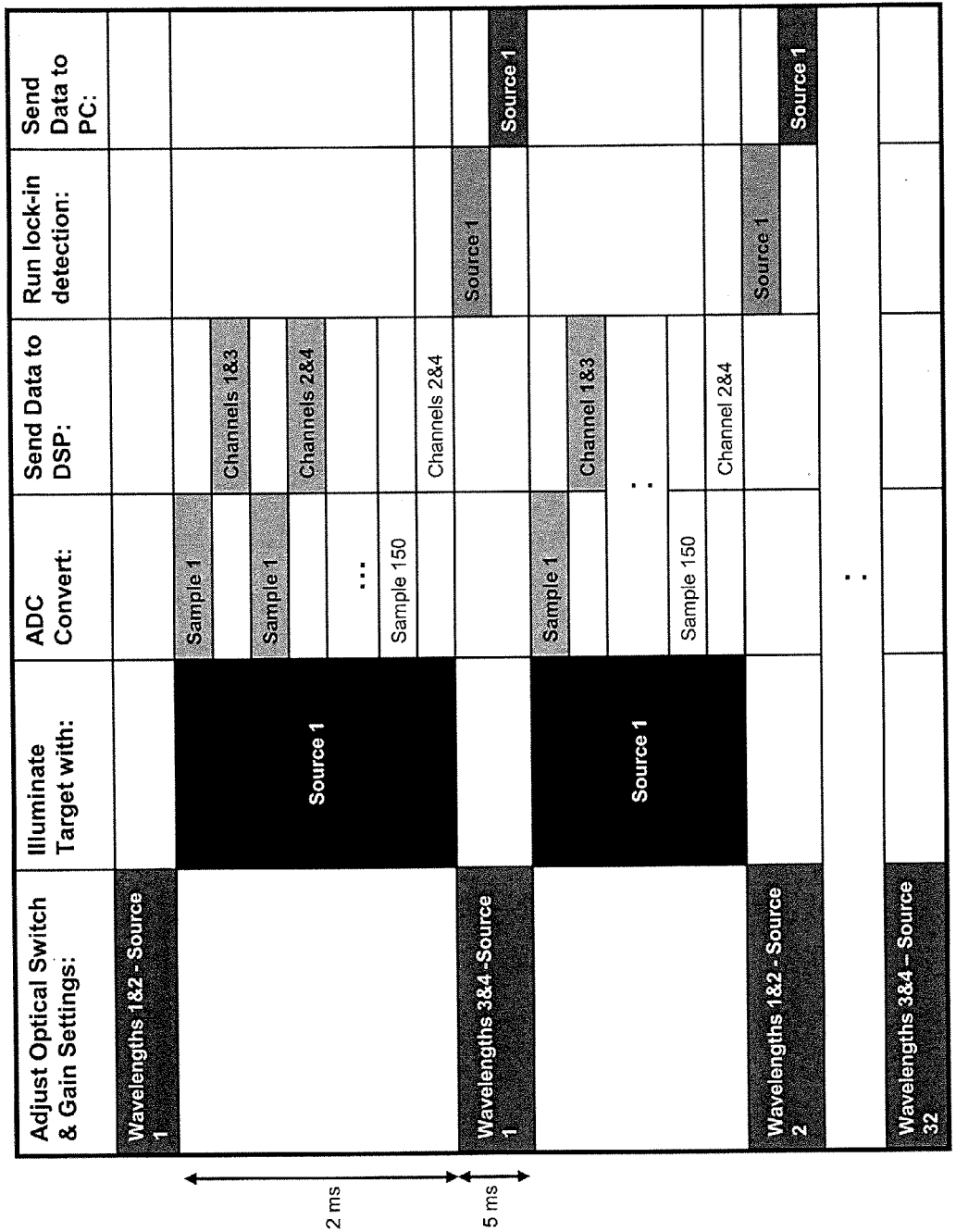
FIG. 18 is an imaging timing sequence diagram in accordance with one embodiment of the disclosed subject matter.

An example of a timing sequence 1800 is illustrated in FIG. 18. First, the switch subsystem 1550 is adjusted to source (n), and the gain setting is updated. In the meantime, the DSP module 1592 performs demodulation and filtering for source (n−1) and sends amplitude data for source (n−1) to the host computer 1510. The tissue is illuminated with the source (n). In the meantime, the data for source (n) is digitized and sent to the DSP module 1592 for further processing.

In some embodiments, for example, a system employing 4 separate component wavelengths and 32 source fibers, allocates 5 ms for adjusting the switch subsystem 1550 and updating the gain setting and 2 ms for the processing of the data, thereby bringing the time to acquire the data for one source and one set of wavelengths (e.g., from channels 1 and 3 or channels 2 and 4) to total of 7 ms. Acquiring a full image frame from all 32 source fibers and the two wavelength sets takes (7 ms)*(2)*(32)=448 ms, resulting in 2.23 frames per second: This imaging frame rate can be increased as the maximum switching time of the switch subsystem 1550 improves.

The dynamic range of a breast imaging system is important due to the potentially large geometries creating a number of scales of measurement. In order to handle the smallest measurements from the furthest source-detector pairs and the largest measurements from the closest source-detector pairs, there is a gain setting for each source-detector pair. These gain settings are automatically determined through testing the amplitude of the signal at each gain setting in order to select the optimal setting.

With gain settings ranging from 1 to $10^7$ and an analog to digital converter with 16 bits of precision, for instance, a dynamic range of $20*\log(2^{16})+20*\log(10^7)=236$ dB can be achieved. Table 2 below summarizes the comparison between the system 1500 and two other different imaging systems. The first of the two imaging systems is DYNOT imager by Schmitz et al., and the second system is a digital instrument designed for dynamic small animal imaging developed by Lasker et al.

TABLE 2

Summary and Comparison of Systems Characteristics

| Parameter | DYNOT | Small Animal Imager | Breast Digital Imager |
|---|---|---|---|
| Mode of Operation | CW | CW | CW |
| Number of Sources | 25 | 16 | 64 |
| Number of Detectors | 32 | 32 | 128 |
| Number of Wavelengths | 1-4 | 1-2 | 1-4 |
| Dynamic Range | 180 dB | 190 dB | 236 dB |
| Data Points per Frame | 3200 | 1024 | 16 384 |
| Data Rate | 8640 Points/s | 9216 Points/s | 32 864 Points/s |
| Acquisition Time | 0.37 sec. | 0.11 sec. | 0.45 sec. |
| Frame Rate | 2.7 Frames/s | 9.09 Frames/s | 2.23 Frames/s |

Although the disclosed subject matter has been described and illustrated in the foregoing illustrative embodiments, it is understood that the present disclosure has been made only by way of example, and that numerous changes in the details of implementation of the disclosed subject matter can be made without departing from the spirit and scope of the disclosed subject matter, which is only limited by the claims which follow. Features of the disclosed embodiments can be combined and rearranged in various ways.

What is claimed is:

1. A method for imaging tissue using diffuse optical tomography with digital detection, the method comprising:
    directing at the tissue a plurality of amplitude modulated optical signals from a plurality of optical signal sources illuminating the tissue at a plurality of locations;
    detecting a resulting plurality of attenuated optical signals exiting the tissue to obtain a plurality of analog signals containing diffuse optical tomographic information;
    converting the analog signals into digital signals using an analog-to-digital converter;
    recovering the tomographic information from the digital signals using a digital signal processor-based detection module that performs digital detection, the detection module comprising a master digital signal processing subsystem configured to receive and process a portion of the digital signals from the analog-to-digital converter, and at least one slave digital signal processing subsystem configured to receive and process a remainder of the digital signals from the analog-to-digital converter, the processing of the digital signals including demodulating the digital signals, wherein the master digital signal processing subsystem controls the at least one slave digital signal processing subsystem by providing timing and control signals to the slave digital signal processing subsystem for processing the digital signals, the control signals including signals to control an input and an output of digital data from the slave digital signal processing subsystem; and
    transmitting the recovered tomographic information in digital form to a host computer for display.

2. The method of claim 1, wherein the at least one slave digital signal processing subsystem processes all of the digital signals.

3. The method of claim 1, wherein the master digital signal processing subsystem controls the at least one slave digital signal processing subsystem by providing at least one timing signal for the processing of the digital signals.

4. The method of claim 1, wherein the amplitude modulated optical signals comprise optical signals at a plurality of wavelengths.

5. The method of claim 4, wherein the optical signals are time and frequency multiplexed.

6. The method of claim 5, wherein an optical signal of a first wavelength and an optical signal of a second wavelength are amplitude-modulated at a first frequency and a second frequency, respectively, at a first time, and an optical signal of a third wavelength and an optical signal of a fourth wavelength are amplitude-modulated at the first frequency and the second frequency, respectively, at a second time.

7. The method of claim 1, wherein the master digital signal processing subsystem and at least one slave digital signal processing subsystem each comprise a programmable logic device that controls processing of the digital signals.

8. The method of claim 7, wherein the master digital signal processing subsystem and at least one slave digital signal processing subsystem each comprise a digital signal processor that controls the corresponding programmable logic device.

9. The method of claim 7, wherein the analog signals are amplified by programmable gain amplifiers controlled by the programmable logic devices.

10. The method of claim 7, wherein the programmable gain amplifiers are controlled by the programmable logic device of the master digital signal processing subsystem.

11. The method of claim 7, wherein the programmable logic device of the master digital signal processing subsystem supplies timing signals to analog-to-digital converters that convert the plurality of analog signals into digital signals.

12. The method of claim 7, wherein the programmable logic device of the master digital signal processing subsystem controls the optical signal sources.

13. The method of claim 1, wherein the digital detection comprises:
    multiplying the digital signals by corresponding in-phase reference signals to obtain in-phase signal components, the corresponding in-phase reference signals having the corresponding frequencies;
    multiplying the digital signals by corresponding quadrature reference signals to obtain quadrature signal components, the quadrature reference signal having the corresponding frequencies;
    passing the in-phase signal components through an averaging filter;
    passing the quadrature signal components through the averaging filter;
    computing signal amplitudes based on the filtered in-phase signal components and the filtered quadrature signal components, the signal amplitudes being representative of the tomographic information; and
    outputting the demodulated signal amplitudes.

14. The method of claim 1, wherein the tissue comprises breast tissue.

15. The method of claim 14, wherein a plurality of amplitude modulated optical signals is directed at both breasts simultaneously.

16. The method of claim 1, wherein the tissue comprises brain tissue.

17. The method of claim 16, wherein a plurality of amplitude modulated optical signals is directed at both brain hemispheres simultaneously.

18. The method of claim 1, wherein the tissue comprises extremity tissues.

19. The method of claim 18, wherein a plurality of amplitude modulated optical signals is directed at both legs simultaneously.

20. The method of claim 18, wherein a plurality of amplitude modulated optical signals is directed at both arms simultaneously.

21. The method of claim 1, wherein the plurality of amplitude modulated optical signal is directed at the tissue and the resulting plurality of attenuated optical signals exiting the tissue is detected while a stimulus is applied to the tissue of a patient.

22. The method of claim 21, wherein the stimulus is applied by having the patient perform the Valsalva maneuver.

23. The method of claim 21, wherein the stimulus is applied by applying a mechanical pressure to the tissue.

24. The method of claim 21, wherein the stimulus is applied by having the patient breath a determined concentration of oxygen.

25. A system for imaging tissue using diffuse optical tomography with digital detection, the system comprising:
a light delivery subsystem configured to direct at the tissue a plurality of amplitude modulated optical signals from a plurality of optical signal sources illuminating the tissue at a plurality of locations; and
a light detection subsystem comprising:
at least one detector configured to detect a resulting plurality of attenuated optical signals exiting the tissue to obtain a plurality of analog signals containing diffuse optical tomographic information;
at least one analog-to-digital converter configured to convert the analog signals into digital signals; and
a digital signal processor-based detection module configured to perform digital detection to recover the tomographic information from the digital signals and transmit the recovered tomographic information in digital form to a host computer for display, wherein the processor-based detection module comprises a master digital signal processing subsystem and at least one slave digital signal processing subsystem the master digital signal processing subsystem processes a portion of the digital signals and the at least one slave digital signal processing subsystem processes a remainder of the digital signals, the processing of the digital signals including demodulating the digital signals, and wherein the master digital signal processing subsystem controls the at least one slave digital signal processing subsystem by providing timing and control signals to the slave digital signal processing subsystem for processing the digital signals, the control signals including signals to control an input and an output of digital data from the slave digital signal processing subsystem.

26. The system of claim 25, wherein the at least one slave digital signal processing subsystem processes all of the digital signals.

27. The system of claim 25, wherein the master digital signal processing subsystem controls the at least one slave digital signal processing subsystem by providing at least one timing signal for the processing of the digital signals.

28. The system of claim 25, wherein the amplitude modulated optical signals comprise optical signals at a plurality of wavelengths.

29. The system of claim 28, wherein the optical signals are time and frequency multiplexed.

30. The system of claim 29, wherein an optical signal of a first wavelength and an optical signal of a second wavelength are amplitude-modulated at a first frequency and a second frequency, respectively, at a first time, and an optical signal of a third wavelength and an optical signal of a fourth wavelength are amplitude-modulated at the first frequency and the second frequency, respectively, at a second time.

31. The system of claim 25, wherein the master digital signal processing subsystem and at least one slave digital signal processing subsystem each comprise a programmable logic device that controls processing of the digital signals.

32. The system of claim 31, wherein the master digital signal processing subsystem and at least one slave digital signal processing subsystem each comprise a digital signal processor that controls the corresponding programmable logic device.

33. The system of claim 31, wherein the analog signals are amplified by programmable gain amplifiers controlled by the programmable logic devices.

34. The system of claim 31, wherein the programmable gain amplifiers are controlled by the programmable logic device of the master digital signal processing subsystem.

35. The system of claim 31, wherein the programmable logic device of the master digital signal processing subsystem supplies timing signals to analog-to-digital converters that convert the plurality of analog signals into digital signals.

36. The system of claim 31, wherein the programmable logic device of the master digital signal processing subsystem controls the optical signal sources.

37. The system of claim 25, wherein the digital detection comprises:
multiplying the digital signals by corresponding in-phase reference signals to obtain in-phase signal components, the corresponding in-phase reference signals having the corresponding frequencies;
multiplying the digital signals by corresponding quadrature reference signals to obtain quadrature signal components, the quadrature reference signal having the corresponding frequencies;
passing the in-phase signal components through an averaging filter;
passing the quadrature signal components through the averaging filter;
computing signal amplitudes based on the filtered in-phase signal components and the filtered quadrature signal components, the signal amplitudes being representative of the tomographic information; and
outputting the demodulated signal amplitudes.

38. The system of claim 25, wherein the tissue comprises breast tissue.

39. The system of claim 38, wherein a plurality of amplitude modulated optical signals is directed at both breasts simultaneously.

40. The system of claim 25, wherein the tissue comprises brain tissue.

41. The system of claim 40, wherein a plurality of amplitude modulated optical signals is directed at both brain hemispheres simultaneously.

42. The system of claim 25, wherein the tissue comprises extremity tissues.

43. The system of claim 42, wherein a plurality of amplitude modulated optical signals is directed at both legs simultaneously.

44. The system of claim 43, wherein a plurality of amplitude modulated optical signals is directed at both arms simultaneously.

45. The system of claim 25, wherein the plurality of amplitude modulated optical signal is directed at the tissue and the resulting plurality of attenuated optical signals exiting the tissue is detected while a stimulus is applied to the tissue of a patient.

46. The system of claim 45, wherein the stimulus is applied by having the patient perform the Valsalva maneuver.

47. The system of claim 45, wherein the stimulus is applied by applying a mechanical pressure to the tissue.

48. The system of claim 45, wherein the stimulus is applied by having the patient breath pure oxygen.

49. The system of claim 25, wherein the recovered tomographic information is transmitted in digital form to the host computer via a Universal Serial Bus.

\* \* \* \* \*